United States Patent
Pavlin

(10) Patent No.: US 8,119,741 B2
(45) Date of Patent: *Feb. 21, 2012

(54) POLYAMIDE-POLYETHER BLOCK COPOLYMER

(75) Inventor: Mark S. Pavlin, Savannah, GA (US)

(73) Assignee: Arizona Chemical Company, LLC, Jacksonville, FL (US)

( * ) Notice: Subject to any disclaimer, the term of this patent is extended or adjusted under 35 U.S.C. 154(b) by 165 days.

This patent is subject to a terminal disclaimer.

(21) Appl. No.: 12/326,849

(22) Filed: Dec. 2, 2008

(65) Prior Publication Data

US 2009/0082460 A1    Mar. 26, 2009

Related U.S. Application Data

(60) Division of application No. 11/753,447, filed on May 24, 2007, which is a continuation of application No. 11/252,441, filed on Oct. 18, 2005, now abandoned, which is a continuation of application No. 10/395,050, filed on Mar. 20, 2003, now Pat. No. 6,956,099.

(51) Int. Cl.
C08L 77/02    (2006.01)

(52) U.S. Cl. .................................................. 525/408

(58) Field of Classification Search .................. 525/408; 424/403, 405
See application file for complete search history.

(56) References Cited

U.S. PATENT DOCUMENTS

| | | |
|---|---|---|
| 3,615,289 A | 10/1971 | Felton |
| 3,622,604 A | 11/1971 | Drawert et al. |
| 3,950,310 A | 4/1976 | Bouboulis |
| 4,062,819 A | 12/1977 | Mains et al. |
| 4,218,351 A | 8/1980 | Rasmussen |
| 4,223,127 A | 9/1980 | Meyer et al. |
| 4,374,741 A | 2/1983 | Rieder |
| 4,398,012 A | 8/1983 | Merrill et al. |
| 4,462,926 A | 7/1984 | Prater et al. |
| 4,471,088 A | 9/1984 | Chiba et al. |
| 4,663,428 A | 5/1987 | Okitu et al. |
| 4,769,285 A | 9/1988 | Rasmussen |
| 4,914,162 A | 4/1990 | Leoni et al. |
| 4,919,934 A | 4/1990 | Deckner et al. |
| 4,940,577 A | 7/1990 | Greenberg et al. |
| 4,952,559 A * | 8/1990 | Login et al. ..................... 512/10 |
| 5,109,054 A | 4/1992 | Smith |
| 5,455,326 A | 10/1995 | Parker |
| 5,665,855 A | 9/1997 | Acevedo et al. |
| 5,770,680 A | 6/1998 | Fischer et al. |
| 5,773,558 A | 6/1998 | Torre |
| 5,783,657 A | 7/1998 | Pavlin et al. |
| 5,804,682 A | 9/1998 | Fischer et al. |
| 5,807,968 A | 9/1998 | Heinrich et al. |
| 5,871,765 A * | 2/1999 | Johnson et al. ............... 424/409 |
| 5,989,697 A | 11/1999 | Gebben |
| 5,998,570 A | 12/1999 | Pavlin et al. |
| 6,045,781 A | 4/2000 | Bungard et al. |
| 6,077,900 A | 6/2000 | Boudreaux et al. |
| 6,117,543 A | 9/2000 | Zaima et al. |
| 6,121,345 A | 9/2000 | Sawada |
| 6,162,860 A | 12/2000 | Anderson et al. |
| 6,174,937 B1 | 1/2001 | Banning et al. |
| 6,194,382 B1 * | 2/2001 | Crain et al. ................... 514/17.5 |
| 6,194,510 B1 | 2/2001 | Anderson et al. |
| 6,242,509 B1 * | 6/2001 | Berger et al. ................. 523/122 |
| 6,268,466 B1 | 7/2001 | MacQueen et al. |
| 6,372,841 B1 | 4/2002 | Anderson et al. |
| 6,399,713 B1 | 6/2002 | MacQueen et al. |
| 6,441,072 B1 | 8/2002 | Havenith et al. |
| 6,497,861 B1 * | 12/2002 | Wang et al. ..................... 424/64 |
| 6,537,335 B1 | 3/2003 | Friars et al. |
| 6,552,160 B2 | 4/2003 | Pavlin |
| 6,870,011 B2 | 3/2005 | MacQueen et al. |
| 6,956,099 B2 | 10/2005 | Pavlin |
| 7,745,546 B2 | 6/2010 | MacQueen et al. |

FOREIGN PATENT DOCUMENTS

| | | |
|---|---|---|
| JP | 03-237131 | 10/1991 |
| WO | 96/14362 | 5/1996 |
| WO | 01/87847 A2 | 11/2001 |
| WO | 02/059181 A2 | 8/2002 |
| WO | 02/092663 A1 | 11/2002 |

OTHER PUBLICATIONS

Office Action as issued in U.S. Appl. No. 10/395,050 on Sep. 3, 2004.
Notice of Allowance as issued in U.S. Appl. No. 10/395,050 on Jun. 8, 2005.
Office Action as issued in U.S. Appl. No. 11/252,441 on Feb. 8, 2006.
Final Office Action as issued in U.S. Appl. No. 11/252,441 on Nov. 24, 2006.

(Continued)

*Primary Examiner* — Gina C Yu

(57) ABSTRACT

Copolymers having linked internal polyether blocks and internal polyamide blocks have advantageous physical properties and solvent-gelling abilities. The copolymer may be prepared from a reaction mixture that contains 1,4-cyclohexane dicarboxylic acid (CHDA) and poly(alkyleneoxy)diamine (PAODA). Optionally, the reaction mixture contains no monofunctional compound reactive with either amine or carboxylic acid groups, however some of this monofunctional compound may be present. Dimer diamine and/or dimer acid may be present in the reaction mixture. A copolymer may also be prepared from a reaction mixture containing dimer acid and at least two diamine compound(s) including PAODA and short-chain aliphatic diamine having 2-6 carbons (SDA), wherein: a) the reaction mixture comprises x grams of PAODA and y grams of SDA, and $x/(x+y)$ is 0.8-0.98; b) the reaction mixture weighs z grams, and $x/z$ is at least 0.25; and c) the reaction mixture contains either no co-diacid, or comprises a small amount of co-diacid, wherein, if the reaction mixture comprises a small amount of co-diacid, then acid equivalents from co-diacid contribute less than 25% of the total acid equivalents present in the reaction mixture.

13 Claims, No Drawings

OTHER PUBLICATIONS

Office Action as issued in U.S. Appl. No. 11/252,441 on Jun. 22, 2007.
Office Action as issued in U.S. Appl. No. 11/753,447 on Jun. 2, 2009.
Notice of Allowance as issued in U.S. Appl. No. 11/753,447 on Dec. 30, 2009.
Office Action as issued in U.S. Appl. No. 11/753,447 dated Jun. 23, 2010.
Office Action as issued in U.S. Appl. No. 12/326,849 on Jul. 7, 2010.
Office Action as issued in U.S. Appl. No. 12/326,846 on Sep. 27, 2010.

* cited by examiner

POLYAMIDE-POLYETHER BLOCK COPOLYMER

REFERENCE TO RELATED APPLICATIONS

This application is a Divisional of and claims priority to U.S. patent application Ser. No. 11/753,447, filed May 24, 2007, which was a Continuation of U.S. patent application Ser. No. 11/252,441, filed Oct. 18, 2005 now abandoned, which was a Continuation of U.S. patent application Ser. No. 10/395,050, filed Mar. 20, 2003, now U.S. Pat. No. 6,956,099, which applications are hereby incorporated by reference.

BACKGROUND OF THE INVENTION

1. Field of the Invention

The present invention is directed to polyamide-polyether block copolymers and the use of polyamide-polyether block copolymers as gellants for liquids in, for example, air fresheners and personal care products.

2. Description of the Related Art

In many commercially important compositions, the consistency of the product is critical to its commercial success. One example is personal care products, which generally contain one or more active ingredients within a carrier formulation. While the active ingredient(s) determine the ultimate performance utility of the product, the carrier formulation is critical to the commercial success of the product in that it largely determines the consistency of the product. The rheology of the carrier or "base" largely determines the manner in which the consumer will apply or use the product. Many commercial and would-be commercial products depend upon the availability of materials called "gelling agents" that have the ability to modify various rheological properties, in order to allow formulation of a successful product.

Products are often desired to be "gels," in that they maintain their shape when undisturbed but flow upon being sheared. Transparent gelled carriers are especially desired by formulators who develop products wherein a colorant is an active ingredient, for example in a lipgloss or rouge, because a transparent carrier (as opposed to an opaque carrier) will minimally, if at all, interfere with the appearance of the colorant. In recent years, consumers have demonstrated an increasing preference for transparent and colorless personal care products such as deodorants and shampoos.

The patent literature contains many descriptions of polyamide compositions, processes for their preparation, and their many uses. The following patents list 1,4-cyclohexane dicarboxylic acid (CHDA) as one of the diacid raw materials that may be used to prepare a polyamide.

U.S. Pat. No. 3,950,310 to Bouboulis (1976), discloses polyamides suitable for use as fibers and molding compounds prepared by reacting a dicarboxylic acid with a cyclohexane-bis(beta-ethylamine). While it is mentioned that the diacid can be CHDA, this is not a preferred diacid.

U.S. Pat. No. 4,218,351 to Rasmussen (1980), discloses the preparation of impact resistant, thermoplastic polyamides having about 58 to about 95 mole % short chain diacid moieties. A list of possible diacids is provided, where the list includes any one of the isomers of CHDA. Other compounds used to make the polyamide are 5 to 30 mol % dimer acid, and 0.25 to 12.5 mole % polyamide-forming oligomer, which can be polyether diamines such as JEFFAMINE™ D-2000. The polyamides are stated to be well suited for use as hot melt adhesives, that is, in adhesive formulations containing no organic solvent.

U.S. Pat. No. 4,223,127 Meyer et al. (1980), discloses polyamides suitable for use in forming fibers, films, and molded objects prepared by reacting a lactam and a dicarboxylic acid with a diamino dicyclohexylmethane. One of the listed dicarboxylic acids is CHDA.

U.S. Pat. No. 4,293,668 to Campbell (1981), discloses polyamides useful for making fibers. The polyamides are prepared from 5-methyl-1,9-nonane diamine and CHDA.

U.S. Pat. No. 4,398,012 to Merrill et al. (1983), discloses copolyamides for use as molding compounds prepared by co-reacting a lactam, a cyclic dicarboxylic acid, and a cyclic diamine. The dicarboxylic acid may be CHDA.

U.S. Pat. No. 4,471,088 to Chiba et al. (1984), discloses copolyamides for use as molding compounds with high rigidity and excellent dimensional stability. These copolyamides are prepared by reacting CHDA and a diamine having 11 to 13 carbon atoms.

U.S. Pat. No. 4,921,932 to Tamura et al. (1990), discloses copolyamides useful as molding compounds prepared by reacting a lactam, a dimerized fatty diacid, a monocarboxylic acid, an optional co-diacid which can be CHDA, and a diamine.

U.S. Pat. No. 5,773,558 to Torre (1998), discloses polyamides useful as molding compounds which having high rigidity, solvent resistance, and high heat resistance. These polyamides are prepared by reacting CHDA with an aliphatic diamine.

The following are exemplary U.S. patents that disclose specific polyamides as gelling agents:

U.S. Pat. No. 3,615,289 to Avon Products (1971), discloses compositions suitable for burning as a candle that consist of a polymerized fatty acid polyamide blended with an alkanolamide and a stearic acid ester.

U.S. Pat. No. 3,819,342 to Avon Products (1974), discloses compositions suitable for burning as a candle that consist of a polymerized fatty acid polyamide blended with a fatty alcohol and having what is described as a "gel-type structure."

U.S. Pat. No. 4,552,693 to Avon Products (1985), discloses compositions suitable for release a fragrance that consist of a polymerized fatty acid polyamide blended with a sulfonamide plasticizer, a fragrance, a surfactant, and a mineral oil. The polyamide comprises 60-65 wt % of the article.

U.S. Pat. No. 5,783,657 to Union Camp Corporation (1998), discloses dimer acid-based polyamide compositions which dissolve in non-polar liquids such as mineral oil and, when cooled to room temperature, form firm, transparent gels. The compositions are specific in requiring that they contain an amount of ester groups and, furthermore, that these esters must be located at the ends of the polymer chain.

U.S. Pat. No. 5,998,570 to Union Camp Corporation (1999), "Ester-Terminated Polyamides Of Polymerized Fatty Acids Useful In Formulating Transparent Gels In Low Polarity Liquids."

U.S. Pat. No. 5,882,363 to The Noville Corp. (1999), discloses compositions suitable for burning as a candle that consists of about 40-70% by weight of a polyamide blended with a 12-hydroxystearic acid ester. The polyamide is not described in detail but is described as a "gellant" and is selected from two classes; nylon terpolymers (DuPont Elvamides) and those made from dimer acid (Henkel Corp. VERSAMID™ resins or Union Camp Corp. UNI-REZ™ resins).

U.S. Pat. No. 6,111,055 to Union Camp Corporation and Bush Boake Allen (2000), contains disclosure directed to polyamide gelling agents useful in preparing candles, flammable objects, etc.

U.S. Pat. No. 6,268,466 (2001) to Arizona Chemical Company, discloses a dimer-acid polyamide which can dissolve in non-polar liquids such as mineral oil and form transparent gels upon cooling. The compositions are specific in requiring that the polymer chains be terminated with tertiary amide groups.

U.S. Pat. No. 6,399,713 to Arizona Chemical Company (2002) discloses polyamide gelling agents (designated PAO-PAs, for poly(alkyleneoxy)-terminated polyamides), consisting of the reaction product of dimer acid, ethylene diamine (EDA), a poly(oxyethylene/propylene)diamine, and a poly(oxyethylene/propylene)monoamine.

Dimer diamine has been described as a component for preparing certain polyamides. For example, U.S. Pat. No. 4,018,731 to Foster Grant Co. (1977), discloses high-impact polyamide resins prepared by reacting an amino carboxylic acid, a lactam, a mixture of a diacid and a diamine, and an amine- or acid-functionalized diolefin polymer.

U.S. Pat. No. 4,018,733 to Raychem Corporation (1977), discloses hot-melt adhesive compositions comprising an acidic ethylene polymer blended with a polyamide. The polyamide is preferably prepared from at least 60% dimer acid and diamine selected from a group of aliphatic diamine including polyether diamines and dimer diamine.

Although certain polyamide resins have the ability to function as gelling agents for organic solvents, there remains a need in the art for compounds that gel liquids, especially polar liquids, to provide gels of varying degrees of hardness and strength, especially at relatively low concentrations of the gelling agent. The present invention is directed to fulfilling this need and provides additional advantages as described more fully herein.

BRIEF SUMMARY OF THE INVENTION

The present invention provides polyamide block copolymers having significant amounts of linked internal polyether blocks and internal fatty blocks, such that the copolymers have advantageous physical properties and gelling abilities. In one aspect, the copolymers of the present invention have a higher softening point than materials known in the art and therefore form gels that retain their form at elevated temperatures better than the gels formed from gellants having relatively lower softening points. Also, the copolymers of the present invention typically function more effectively at low concentrations compared to gellants disclosed in the prior art. Additionally, the preferred copolymers of this invention possess higher molecular weights than prior art gellant polyamides so that their gels, upon evaporation of the bulk gel liquid, yield a tough flexible film. Additionally, the copolymers of the present invention often yield gels with viscoelastic character (i.e., the gelling agents can function as "thickeners" rather than "gellants" in some solvents, especially glycol ethers), as well as soft and hard gels having a more solid-like consistency.

In one aspect, the present invention provides a polyamide-polyether block copolymer. The copolymer has a softening point between 60° C. and 180° C. The copolymer is formed from a reaction mixture, where the reaction mixture comprises one or more diacid compound(s) that include 1,4-cyclohexane dicarboxylic acid (CHDA), and one or more diamine compound(s) that include poly(alkyleneoxy)diamine (PAODA). The reaction mixture does not contain monofunctional compound reactive with either amine or carboxylic acid groups. In one embodiment, the diamine compound(s) further include dimer diamine. In another embodiment, the diacid compound(s) further include polymerized fatty acid.

In another aspect, the present invention provides a polyamide-polyether block copolymer having a softening point between 60° C. and 180° C. The block copolymer is formed from a reaction mixture comprising one or more diacid compound(s) that include 1,4-cyclohexane dicarboxylic acid (CHDA), and one or more diamine compound(s) that include poly(alkyleneoxy)diamine (PAODA). The reaction mixture also contains one or more monofunctional compound(s) that are reactive with carboxylic acid groups. In one embodiment the diamine compound(s) further include dimer diamine. In another embodiment, the diacid compound(s) further include polymerized fatty acid.

In another aspect, the present invention provides a polyether block copolymer having a softening point between 60° C. and 180° C. The copolymer is formed from a reaction mixture comprising one or more diacid compound(s) that include 1,4-cyclohexane dicarboxylic acid (CHDA), and one or more diamine compound(s) that include poly(alkyleneoxy)diamine (PAODA). The reaction mixture also includes one or more monofunctional compound(s) that are reactive with amine groups. In one embodiment the diamine compound(s) further include dimer diamine. In another embodiment, the diacid compound(s) further include polymerized fatty acid.

While the softening point of the resin may be from 60° C. to 180° C., optionally the softening point is between 100° C. and 140° C. As another optional aspect, CHDA may be the only diacid compound present in the above-described reaction mixtures. As a further optional aspect, CHDA provides at least 45% of the acid equivalents attributed to the diacid compound(s) in each of the above-described reaction mixtures. Optionally, when polymerized fatty acid is present in the reaction mixture, the polymerized fatty acid provides less than 25% of the equivalents of the acid groups attributed to the diacid compound(s). In an optional embodiment, the reaction mixture may include a dihydric compound. Poly(alkyleneoxy)dialcohol is the dihydric compound in one aspect of the invention, where optionally, the poly(alkyleneoxy)dialcohol compound is present in the reaction mixture in an amount of less than 40 eq. % of the total equivalents of amine and hydroxyl present in the reaction mixture. Unless otherwise specified, each of the reaction mixtures may contain co-diacid, where in one aspect the co-diacid is selected from the group consisting of adipic acid, sebacic acid, azelaic acid, isophthalic acid, dodecanedioic acid, and 1,3-cyclohexane dicarboxylic acid. In one embodiment, and unless otherwise specified, the PAODA is the only diamine compound present in the reaction mixture. When PAODA is not the only diamine compound present in the reaction mixture, then in one optional aspect the PAODA provides at least 20% of the amine equivalents attributed to the diamine compound(s) present in the reaction mixture. Optionally, the PAODA includes PAODA compounds having molecular weights between 400 and 5,000. Optionally, the diamine compound(s) present in the reaction mixture exclude diamines of the formula $H_2N—R^2—NH_2$ wherein $R^2$ is $C_2$-$C_6$ hydrocarbyl. A small amount of such diamines may be present in the mixture, such that in one aspect wherein the diamine compound(s) include diamines of the formula $H_2N—R^2—NH_2$ wherein $R^2$ is $C_2$-$C_6$ hydrocarbyl, these diamines provide less than 10% of the amine equivalents attributed to diamine compound(s). Optionally, the copolymer of the present invention has a weight average molecular weight of between 10,000 and 40,000, as measured using gel permeation chromatography with polystyrene as reference standards.

Some specific structures for the copolymers that may be prepared according to the present invention are:

A compound of formula (3):

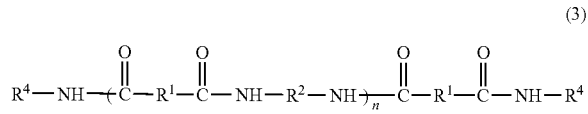

(3)

wherein, in at least one occurrence, $R^1$ is a $C_6$ carbocyclic group; $R^2$ is a polyalkyleneoxide moiety; $R^4$ is selected from a hydrocarbon group having at least 4 carbons and a polyalkyleneoxide moiety having a formula weight of at least 100; and n is an integer of at least 11;

a compound of formula (4):

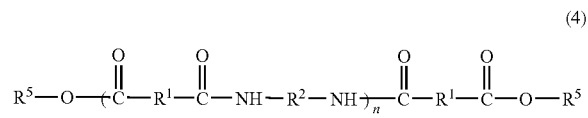

(4)

wherein, in at least one occurrence, $R^1$ is a $C_6$ carbocyclic group; $R^2$ is a polyalkyleneoxide moiety; $R^5$ is selected from a hydrocarbon group having at least 4 carbons and a polyalkyleneoxide moiety having a formula weight of at least 100; and n is an integer of at least 11; and a compound of formula (5):

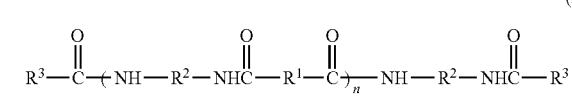

(5)

wherein, in at least one occurrence, $R^1$ is a $C_6$ carbocyclic group; $R^2$ is a polyalkyleneoxide moiety; $R^3$ is a hydrocarbon group having at least 2 carbons; and n Is an integer of at least 11.

In one aspect, the copolymer of the present invention has a softening point between 100° C. and 140° C.; is prepared from a reaction mixture wherein CHDA provides at least 45% of the acid equivalents attributed to diacid compound(s); polymerized fatty acid is present in the reaction mixture, however the components of the polymerized fatty acid provide less than 25% of the equivalents of acid groups attributed to the diacid compound(s), and PAODA provides at least 20% of the amine equivalents attributed to the diamine compound(s).

In another aspect, the present invention provides a polyamide-polyether block copolymer having a softening point between 60° C. and 180° C. formed from a reaction mixture. The reaction mixture comprises one or more diacid compound(s) that include polymerized fatty acid, and at least two diamine compound(s) including poly(alkyleneoxy)diamine (PAODA) and short-chain aliphatic diamine having 2-6 carbons (SDA). This reaction mixture x grams of PAODA and y grams of SDA, such that x/(x+y) is 0.8-0.98. Also, the reaction mixture weighs z grams, such that x/z is at least 0.25. Also, the reaction mixture contains either no co-diacid, or comprises a minor amount of co-diacid, wherein, if the reaction mixture comprises a minor amount of co-diacid, then acid equivalents from co-diacid contribute less than 25% of the total acid equivalents present in the reaction mixture.

Optionally, the softening point of the copolymer is between 100° C. and 140° C.; polymerized fatty acid is the only diacid compound present in the reaction mixture; co-diacid is present in the reaction mixture, however, co-diacid contributes less than 10% of the total acid equivalents present in the reaction mixture; PAODA and SDA together constitute at least 95 wt % of the diamine compounds present in the reaction mixture; the diamine compound(s) include poly(alkyleneoxy)diamine having a molecular weight of at least 400 g/mol; x/z is at least 0.3; and/or x/z is at least 0.4.

The polyamide-polyether block copolymers of the present invention may be used as gelling agents, also known as structuring agents, thickeners, rheological modifiers, or thixotropic agents. For example, in one aspect the polyamide-polyether copolymer is a gelling agent for liquid esters such as methyl soyate, glycol ethers such as dipropylene glycol monomethyl ether, hydroxy-substituted esters such as ethyl lactate. In another aspect, the polyamide-polyether copolymer is a gelling agent for polyesters such as dibutyl adipate.

The present invention also provides compositions that include a polyamide-polyether block copolymer as described herein and a compound or mixture of compounds, where the compound or mixture of compounds is a liquid at room temperature in neat form. Such a composition may be fluid at elevated temperatures and in the form of a gel at a lower temperature, for example, at room temperature. The compound(s) may comprise a functional group, e.g., an ester, alcohol, aromatic ring, ether, halogen, carbonate and/or sulfoxide.

The gels and compositions of the present invention may be formulated into various articles of manufacture. Such articles of manufacture are described more fully below, but include personal care products, paint strippers, air fresheners, medicament applicators, polishes, and the like which are desirably in a gel or thickened state.

These and other aspects of this invention will become apparent upon reference to the following detailed description.

DETAILED DESCRIPTION OF THE INVENTION

The prevent invention is directed to polyamide-polyether block copolymers. As used herein, the term "polyamide" denotes a macromolecule containing a plurality of amide groups, i.e., groups of the formula —NH—C(=O)— and/or —C(=O)—NH—, and the term "polyether" denotes a macromolecule containing a plurality of ether groups, i.e., groups of the formula R—O—R where R represents an organic (carbon-containing) group. Polyamides as a class of polymer are well known in the art, and are commonly prepared via a condensation polymerization process whereby diamines are reacted with dicarboxylic acid (diacids). As discussed below, the copolymers of the present invention are likewise conveniently prepared by reacting diamines with diacids. Polyethers as a class of polymer are also well known, where one type of polyether is commonly prepared by reaction of an alkylene oxide (e.g., ethylene oxide) with an initiating group (e.g., methanol). At present, many polyethers are commercially available that have terminating groups selected from amine, hydroxyl and carboxylic acid. The use of polyethers having two amine terminating groups is used according to the present invention to introduce polyether blocks into a polyamide copolymer. This approach provides blocks of polyether groups within a polyamide copolymer. It has been discovered that copolymers having this structure are broadly useful in many compositions, particularly including compositions where the copolymer acts to thicken or gel a solvent.

In the polyamide-polyether block copolymers, nearest amide groups are separated by either alkylene groups or polyether (i.e., poly(alkyleneoxy)) groups. As used herein, the term "alkylene" refers to a divalent hydrocarbon radical group (i.e., hydrocarbyl diradical) containing exclusively C—C and C—H single bonds, while "hydrocarbon" refers to any molecular structural domain containing exclusively carbon and hydrogen atoms. As used herein, the term "polyether" refers to a divalent radical the includes a plurality of, i.e., at least two, ether groups, where an ether group has the formula R—O—R and R represents alkylene groups and O represents oxygen. Polyether groups are also referred to herein a poly(alkylene)oxide groups. The structure of polyether groups may also be represented as $(O-R)_n$, where "n" represents a number of repeating O—R groups. The polyamide-polyether copolymers of the present invention contain at least one internal polyether group, i.e., a polyether group that is flanked by two amide groups.

The polyamide-polyether block copolymers of the present invention contain a polyether block, and more specifically, a polyether block flanked by two amide groups. In one aspect of the invention, two amide groups of the polyamide-polyether copolymer also flank a 1,4-substituted cyclohexyl diradical. It has been surprisingly found that the copolymers containing this particular combination of groups, i.e., cyclohexyl diradicals and polyether diradicals, each flanked by amide groups, provide an effective gellant for liquids, particularly polar liquids. However, in order for the copolymers to be effective gellants, it is necessary to be able to prepare a solution containing the copolymer and a solvent to be gelled, and this is accomplished when the softening point of the copolymer is not excessively high. According to the present invention, the softening point of the inventive copolymer is between 60° C. and 180° C. As discussed in further detail below, when the softening point is below about 60° C., the copolymer typically provides very little thickening or gelling function to a composition containing the copolymer and a solvent. When the softening point is above about 180° C., the copolymer is so high melting that it is very difficult to prepare a solution of the copolymer and a solvent to be gelled. Accordingly, the preferred softening point range for the copolymer is 60-180° C.

The 1,4-substituted cyclohexyl diradicals are conveniently introduced into the polyamide-polyether copolymer by use of 1,4-cyclohexane dicarboxylic acid (CHDA), while the polyether diradicals are conveniently introduced into the polyamide-polyether copolymer by use of poly(alkyleneoxy)diamine (PAODA). It has been discovered that the use of CHDA as the diacid component of a copolymer-forming mixture yields a polyamide-polyether of relatively higher softening point than virtually any other commercially-available diacid. It has also been found that high levels of poly(alkyleneoxy) moieties (PAO moieties) can be used in the polyamide-polyether reaction admixture while still maintaining a very high softening point for the copolymer. As a result, these copolymers are compatible with polar liquids, and can be used to form relatively hard gels from polar liquids, such gelation being maintained even at high temperatures.

A further surprising feature of the copolymers of this invention is that they require no special terminal groups; i.e., the polymers need not be terminated by an ester group, tertiary amide group, or poly(alkyleneoxy)-substituted amide. They may, then, be of high molecular weight, have residual acid groups as termini or residual amine groups as termini. In one aspect of the invention, the reaction mixture that is used to prepare the polyamide-polyether block copolymer does not include any monofunctional reactants that would react with either amine or carboxylic acid groups.

Accordingly, in one aspect, the present invention provides a polyamide-polyether block copolymer having a softening point between 60° C. and 180° C. formed from a reaction mixture comprising one or more diacid compound(s) including 1,4-cyclohexane dicarboxylic acid (CHDA), and one or more diamine compound(s) including poly(alkyleneoxy)diamine (PAODA), wherein the reaction mixture contains no monofunctional reactant, i.e., reactant that is monofunctional and that will react with either carboxylic acid groups or amine groups.

While the copolymers of the present invention do not require any terminating reaction, i.e., reaction with monofunctional reactant, some amount of terminating reaction may be used in preparing these copolymers. Thus, in another aspect, the present invention provides a polyamide-polyether block copolymer having a softening point between 60° C. and 180° C. formed from a reaction mixture comprising one or more diacid compound(s) including 1,4-cyclohexane dicarboxylic acid (CHDA), and one or more diamine compound(s) including poly(alkyleneoxy)diamine (PAODA), wherein the reaction mixture contains an amount, preferably a minor amount, of monofunctional reactant, i.e., reactant that is monofunctional and that will react with either carboxylic acid groups or amine groups. These monofunctional reactants are described in detail below.

Thus, in one aspect, the present invention provides a polyamide-polyether block copolymer having a softening point between 60° C. and 180° C. formed from a reaction mixture comprising one or more diacid compound(s) that include 1,4-cyclohexane dicarboxylic acid (CHDA), one or more diamine compound(s) that include poly(alkyleneoxy)diamine (PAODA), and one or more monofunctional compounds that are reactive with carboxylic acid groups. In another aspect, the present invention provides a polyamide-polyether block copolymer having a softening point between 60° C. and 180° C. formed from a reaction mixture comprising one or more diacid compound(s) that include 1,4-cyclohexane dicarboxylic acid (CHDA), one or more diamine compound(s) that include poly(alkyleneoxy)diamine (PAODA), and one or more monofunctional compounds that are reactive with amine groups. As will be discussed in further detail below, in additional aspects the present invention is directed to the use of the copolymers identified herein as gellants of organic liquids, and in further aspects the present invention is directed to compositions of the copolymers identified herein in admixture with an organic solvent, the composition preferably being a gelled composition where the copolymer has provided structure to the solvent.

In various optional aspects of the invention, the monofunctional reactant is present in the reaction mixture in a "minor amount". The term "minor amount" refers to the situation where:

a) the monofunctional reactant(s) present in the reaction mixture comprise either a single functional group that is reactive with an acid group of the diacid compound (an acid-reactive group) or a single functional group that is reactive with an amine group of the diamine compound (an amine-reactive group);

b) the reaction mixture contains equivalents of acid groups contributed by the monoacid (if present) and diacid compounds (the acid groups), equivalents of amine groups contributed by the monoamine (if present) and diamine compounds (the amine groups), and at least one of i) equivalents of the acid-reactive group(s) selected from monoamine and monoalcohol, and ii) an equivalents of the amine-reactive group(s) selected from monoacid compounds;

c) the reaction mixture is characterized by a first ratio and a second ratio, the first ratio being the equivalents of the acid-reactive groups to the equivalents of the acid groups, and the second ratio being the equivalents of the amine-reactive groups to the equivalents of the amine groups; and d) where a minor amount of monofunctional reactant is present in the reaction mixture when the sum of the first ratio and the second ratio is less than 0.09.

The value of 0.09 is selected according to the present invention in order to afford a relatively small amount of termination, which is preferred in order for the copolymers to have good gelation properties. As stated above, this sum may be 0.0 when there is no termination. In various additional aspects of the invention, this sum is 0.08, 0.07, 0.06, 0.05, 0.04, 0.03, 0.02 and 0.02.

In general, very little monofunctional reactant is required in order to prepare a copolymer useful as a gelling agent. In various aspects of the invention, the monofunctional reactant contributes less than 10%, or less than 9%, or less than 8%, or less than 7%, or less than 6%, or less than 5%, or less than 4%, or less than 3%, or less than 2%, or less then 1%, or less than 0.5% of the total weight of the copolymer-forming reactants.

In one aspect, the polyamide-polyether block copolymer of the invention is formed from a reaction mixture that contains no monofunctional compound reactive with either amine or carboxylic acid groups. For clarification it is explained that this condition refers to fact that no pure, or nearly pure, monofunctional compound reactive with either amine or carboxylic acid groups is added to the reaction mixture. The specification that the reaction mixture contains no functional compound reactive with either amine or carboxylic acid groups is not intended to preclude the use of reactants that contain a minor amount of monofunctional compound as an impurity.

For example, the standard commercial grade of PAODA may be contaminated with a percent or two of PAOMA. However, the use of such impure PAODA is not considered to be the addition of monofunctional compound to the reaction mixture.

Likewise, "polymerized fatty acid" is considered to refer to a difunctional acid material, even though the polymerized fatty acid of commerce may be contaminated with small amount(s) of monomeric fatty acid and/or some trimer acid. Because "polymerized fatty acid" contains such a large amount of dimer acid, polymerized fatty acid is frequently referred to in commerce as "dimer acid", even though it is often not 100% pure dimer acid. Thus, the terms "polymerized fatty acid" and "dimer acid" and "dimer" are often used synonymously in the art, and that convention will be used herein. However, even though the "dimer acid" or "polymerized fatty acid" (where these two terms are referring to the same material) contains some monomeric fatty acid and/or trimer acid, for purposes of calculating equivalents and weight percentages, the polymerized fatty acid is considered to be composed entirely of difunctional acid material, so long as the difunctional acid material constitutes at least 75 wt % of the total weight of the composition.

The use of commercial grade dimer acid (polymerized fatty acid) as a component of a reaction mixture is not considered to add monomeric fatty acid to the reaction mixture, even though some small amount of monomeric fatty acid may be in admixture with the dimer acid. The specification sheets of the following commercial "dimers" state the indicated levels of monomer and trimer present in admixture with the "dimer acid": PRIPOL™ 1017 dimer (Unichema) has 1-3% monomer, 75-80% dimer and 18-22% trimer; PRIPOL™ 1012 dimer (Unichema) has 0.1% monomer, 97% min. dimer and 18-22% trimer; PRIPOL™ 1013 dimer (Unichema) has 0.1% monomer, 93-98% dimer and 1% max. trimer, with 2% max of "other"; PRIPOL™ 1006 dimer (Unichema) has 0.4% max monomer, 93-98% dimer and 24% max. trimer; EMPOL™ 1008 dimer (Cognis) has 2-6% monomer, 90-98% dimer and 1-5% trimer; EMPOL™ 1012 dimer (Cognis) has 1-7% monomer, 88-95% dimer and 1-5% trimer; EMPOL™ 1016 dimer (Cognis) has 4% monomer, 80% dimer and 16% trimer. These percent values are in terms of weight percent, based on the total weight of the commercial product. According to the present invention, the use of these or other similar commercial grades of dimer in a reaction mixture is not to be construed to provide for the use of monofunctional reactant reactive with amine or carboxylic acid groups. Thus, for purposes of the present invention, all of the acid functionality provided by a commercial grade dimer is considered to derive from difunctional material.

To reiterate, the condition that the reaction mixture does not contain any monofunctional compound reactive with acid or amine groups is not intended to mean that each of the components of the reaction mixture must be 100% pure and cannot contain even the slightest trace of monofunctional compound reactive with acid or amine groups.

On the other hand, when it is intended that the reaction mixture does not contain any terminating reactant, i.e., when no monofunctional reactant that is reactive with acid or amine groups should be present in the reaction mixture, the reactants should be largely pure and free of impurities that are terminating reactants or else the copolymer will be inadvertently terminated by the impurities. Accordingly, polymerized fatty acid will be considered to contain only difunctional acid so long as the difunctional acid content of the polymerized fatty acid is at least 75 wt % of the total weight of the composition. Preferably, however, the difunctional acid content of the polymerized fatty acid is at least 80 wt %, or more preferably at least 85 wt %, or still more preferably at least 90 wt % of the total weight of the composition.

In addition to having the difunctional acid content of the polymerized fatty acid be at least 75 wt %, the contamination from monomeric fatty acid (i.e., fatty acid with 18 carbon atoms) is preferably less than about 7 wt % of the total weight of the polymerized fatty acid. Preferably, when no monofunctional reactant is present in the reaction mixture, and yet polymerized fatty acid is added to the reaction mixture, the polymerized fatty acid contains less than 5 wt % monomeric fatty acid, and more preferably contains less than or equal to 3 wt % monomeric fatty acid. Polymerized fatty acid having less than or equal to 3 wt % monomeric fatty acid is a standard grade of commercially available "dimer acid". Likewise with each of the other difunctional reactants, they preferably contain less than 7 wt % impurity that is monofunctional and reactive with amine or carboxylic acid groups. When the difunctional reactant contains more than about 10 wt % of reactive monofunctional material, then this monofunctional material begins to exert a noticeable effect on the properties of the product copolymer, and the terminating effect of these reactive monofunctional material should be considered in calculating the desired stoichiometry of the reactants.

When polymerized fatty acid is a component of a reaction mixture, the content of trimer acid in combination with the dimer acid should be considered. The trimer acid, being a trifunctional material, tends to cause crosslinking to occur, and at the very least causes a more rapid increase in copolymer molecular weight than does pure dimer acid. Accordingly, the amount of trimer acid present in admixture with the dimer acid is preferably minimized. A dimer acid with a high trimer acid content may be used in the present invention, however, some monofunctional reactant that is reactive with the trimer acid; e.g., monoamine or monoalcohol, is preferably used as a co reactant in order to minimize the formation of high molecular weigh copolymer. A polymerized fatty acid having 2-6% monomer acid, 90-98% dimer acid and 1-5% trimer acid is a preferred "dimer" of the present invention.

In one aspect of the invention, monoamine is present among the reactants. In various aspects when monoamine is present among the reactants, the amine equivalents from monoamine contribute less than 10%, or less than 9%, or less than 8%, or less than 7%, or less than 6%, or less than 5%, or less than 4%, or less than 3%, or less than 2%, or less than 1% of the total amine equivalents (i.e., equivalents of amine contributed by monoamine, diamine, and any other amine-containing compound) present in the reaction mixture. In various other aspects when monoamine is present among the reactants, the amine equivalents from monoamine contribute less than 10%, or less than 9%, or less than 8%, or less than 7%, or less than 6%, or less than 5%, or less than 4%, or less than 3%, or less than 2%, or less than 1% of the total equivalents of amine-reactive groups present in the reaction mixture, where carboxylic acid is an amine-reactive group that will necessarily be present in the reaction mixture.

In one aspect of the invention, monoalcohol is present among the reactants. In various other aspects when monoalcohol is present among the reactants, the hydroxyl equivalents from monoalcohol contribute less than 10%, or less than 9%, or less than 8%, or less than 7%, or less than 6%, or less than 5%, or less than 4%, or less than 3%, or less than 2%, or less than 1% of the total equivalents of alcohol and amine (i.e., equivalents of amine contributed by monoamine, diamine, and any other amine-containing compound, plus equivalents of hydroxyl contributed by alcohols) present in the reaction mixture. In various other aspects when monoalcohol is present among the reactants, the hydroxyl equivalents from monoalcohol contribute less than 10%, or less than 9%, or less than 8%, or less than 7%, or less than 6%, or less than 5%, or less than 4%, or less than 3%, or less than 2%, or less than 1% of the total equivalents of hydroxyl-reactive groups present in the reaction mixture, where carboxylic acid is a hydroxyl-reactive group that will necessarily be present in the reaction mixture.

In one aspect, monoacid is present among the reactants. In various aspects when monoacid is present among the reactants, the acid equivalents from monoacid contribute less than 10%, or less than 9%, or less than 8%, or less than 7%, or less than 6%, or less than 5%, or less than 4%, or less than 3%, or less than 2%, or less than 1% of the total acid equivalents (i.e., equivalents of acid contributed by monoacid, diacid, and any other acid-containing compound) present in the reaction mixture. In various other aspects when monoacid is present among the reactants, the acid equivalents from monoacid contribute less than 10%, or less than 9%, or less than 8%, or less than 7%, or less than 6%, or less than 5%, or less than 4%, or less than 3%, or less than 2%, or less than 1% of the total equivalents of acid-reactive groups present in the reaction mixture, where amine is both an acid-reactive group that will necessarily be present in the reaction mixture.

It is possible to include more than one-type of monofunctional reactant in the reaction mixture. For instance, monoamine and monoacid, or monoamine and monoalcohol, or monoacid and monoalcohol, or monoacid and monoamine and monoalcohol. When mixtures of monofunctional reactant are utilized in the reaction mixture, then in various aspects of the invention, the monofunctional reactants, in total, contribute less than 10%, or less than 9%, or less than 8%, or less than 7%, or less than 6%, or less than 5%, or less than 4%, or less than 3%, or less than 2%, or less than 1% of the reactive equivalents present in the reaction mixture (i.e., reactive equivalents from any source, including, e.g., diacid, diamine, monoacid, monoamine, monoalcohol).

For example, in one aspect of the invention the reaction mixture includes both monoamine and monoalcohol. In this case, then in various aspects of the invention the total of the hydroxyl equivalents from monoalcohol and amine equivalents from monoamine contribute less than 10%, or less than 9%, or less than 8%, or less than 7%, or less than 6%, or less than 5%, or less than 4%, or less than 3%, or less than 2%, or less than 1% of the sum of the total amine equivalents (i.e., equivalents of amine contributed by monoamine, diamine, and any other amine-containing compound) and the total hydroxyl equivalents (i.e., equivalents of hydroxyl contributed by alcohols) present in the reaction mixture. In various other aspects when both monoamine and monoalcohol are present among the reactants, the total of the hydroxyl equivalents from monoalcohol and amine equivalents from monoamine contribute less than 10%, or less than 9%, or less than 8%, or less than 7%, or less than 6%, or less than 5%, or less than 4%, or less than 3%, or less than 2%, or less than 1% of the total equivalents of amine-reactive groups and alcohol-reactive groups present in the reaction mixture, where carboxylic acid is both an amine-reactive group and a hydroxyl-reactive groups that will necessarily be present in the reaction mixture.

Specific monofunctional reactants, e.g., specific monoamines, monoalcohols and monocarboxylic acid, are described in detail below.

Typically, polymers are prepared from a reaction mixture, where the reaction mixture contains the chemicals that react together to form the polymer. As used herein, the term "reaction mixture" refers to all of the chemicals, and all of the amounts of those chemicals, that are used to form the polymer. For instance, a polymer may be prepared by reacting chemicals "a" and "b", and then adding chemical "c" to the reaction product(s) of chemicals "a" and "b" (the reaction products may be abbreviated as "ab" for convenience). The reaction mixture, as that term is used herein, refers to a hypothetical mixture of chemicals "a", "b" and "c" even though, in fact, each of those chemicals may be not present together at any one time because chemicals "a" and "b" reacted to form a product ("ab") and are therefore not present when chemical "c" is added to the reaction flask. Solvents may be present during the formation of the copolymer, however, because solvents do not become incorporated into the structure of the copolymer, solvents are not included within the term "reaction mixture".

In one embodiment of the present invention, a polyamide-polyether copolymer is formed from a reaction mixture that includes 1,4-cyclohexane dicarboxylic acid and a poly(alkyleneoxy)diamine. As used herein, the terms 1,4-cyclohexane dicarboxylic acid and poly(alkyleneoxy)diamine refer to both the chemicals per se as well as reactive equivalents thereof. For example, reactive equivalents of 1,4-cyclohexane dicarboxylic acid include the corresponding salt forms, acid halides and short-chain esters. Reactive equivalents of poly (alkyleneoxy)diamine include the corresponding salt forms and short-chain amides. Either the chemicals per se, or their reactive equivalents, may be used to prepare the polyamide-polyether copolymers of the present invention.

The components of the reaction mixture should be selected, in terms of structure and quantity, so as to provide a copolymer having a softening point between about 60° C. and about 180° C. As mentioned previously, when the softening point of the polyamide-polyether copolymer is too low, the gel formed from the polyamide and solvent is often undesirably soft, i.e., the gelled composition does not demonstrate adequate gelled properties unless chilled to well below typical room temperatures. For most purposes, a softening point of at least 60° C. is typically needed in order for the copolymer to impart significant gelled properties to a copolymer/solvent composition. When the softening point becomes to high, it is very difficult to dissolve the copolymer in a solvent, where this dissolution process is preferably accomplished by melting the copolymer in the presence of the solvent. Accordingly, a softening point within the range of about 60° C. and about 180° C. is preferred.

In various aspects of the invention, the softening point of the copolymer is at least 65° C., or at least 70° C., or at least 75° C., or at least 80° C., or at least 85° C., or at least 90° C., or at least 95° C., or at least 100° C., or at least 105° C., or at least 110° C., or at least 115° C., or at least 120° C. In various other aspects, the softening point of the copolymer is not more than 170° C., or not more than 160° C., or not more than 150° C., or not more than 140° C., or not more than 130° C. Thus, for example, the present invention provides polyamide-polyether copolymers having softening points between 60-180° C., where the lower limit of this range may be replaced with any of the values of and between 65-120° C. as set forth above, and independently, the upper limit of this range may be replaced with any of the values of 130-170° C. as also set forth above. In a preferred aspect of the invention, the copolymer has a softening point between 110° C. and 140° C.

Softening point, which may also be referred to as melting point, may be measured by the so-called "ring and ball" method, which is the subject of ASTM E28 (www.astm.org, West Conshohocken, Pa., USA). Alternatively, a softening point value may be obtained using a Mettler FP80 Central Processor and a Mettler FP83 HT Dropping Point Cell employing a softening point ring. This apparatus is available from Mettler Laboratories (Hightstown, N.J., USA). The melting point values described and reported herein were obtained using either a Mettler FP83HT apparatus or a ring-and ball apparatus.

In general, the softening point of the polyamide-polyether copolymer may be adjusted as described herein, for example, by varying the amount of chain termination, where shorter chains tend to have a lower softening point, by varying the amount of CHDA used in the reaction mixture, where increasing the CHDA amount tends to increase the softening point of the polyamide, and by varying the amount of polyether, where increasing polyether amount tends to decrease the softening point of the copolymer, and by varying the type of polyether, where increasing the (ethyleneoxy) content tends to decrease the softening point relative the (propyleneoxy) content. As the copolymer's softening point increases, it becomes more difficult to dissolve the polyamide in the solvent that is being gelled. However, an increase in the softening point of the polyamide tends to provide for a gelled solvent/copolymer composition that is increasingly stable to high temperatures, i.e., a higher softening point polyamide provides a gelled composition that retains it gelled state at higher temperature. It is generally, although not always desirable that the gelled composition have improved high temperature stability.

The cyclohexyl/polyether-containing polyamide-polyether copolymer is thermoplastic and has both a suitably low softening point of about 60-180° C. and compatibility with an organic liquid such that, upon blending the organic liquid and the copolymer in the presence of adequate heating and shearing, a homogenous blend is created which, upon cooling, is in the form of a gel. Many polyamides of the prior art, designed to be heat-resistant molding compounds, are not suitable as gelling agents either because they have very high melting points, typically over 200° C. which means they cannot be blended with typical organic liquids one needs to gel, or they are entirely incompatible with these liquids.

Both cyclohexane dicarboxylic acids and polyether diamines are standard commercial chemicals that are well known to one of ordinary skill in the art. There are several isomers of cyclohexanedicarboxylic acid. For example, the two carboxylic acid groups can be arranged in a 1,2 (ortho), 1,3 (meta) or 1,4 (para) relationship around the cyclohexyl ring. In addition, the two acid groups may be disposed on the same side of the cyclohexyl ring (cis) or on opposite sides (trans). In a preferred embodiment, the CHDA is 1,4-cyclohexanedicarboxylic acid as obtained from, e.g., Eastman Chemical Company (Kingsport, Tenn., USA) or Aldrich Chemical (Milwaukee, Wis., USA).

Examples of poly(alkyleneoxide) diamines (PAODAS) include, but are not limited to, those having the structural formula:

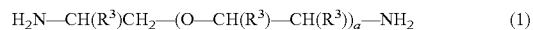

$$H_2N-CH(R^3)CH_2-(O-CH(R^3)-CH(R^3))_a-NH_2 \quad (1)$$

wherein:

$R^3$ at each occurrence is a monovalent radical independently selected from the group consisting of hydrogen and $C_1$ to $C_4$ aliphatic hydrocarbons, and 'a' is up to about 100, preferably about 2 to about 75, more preferably about 8 to about 50. The molecular weight of the PAODA can vary over a wide range, however, when the molecular weight becomes too low then high-melting salts form between the PAODA and the CHDA, where these high-melting salts are difficult to work with in a manufacturing environment. Accordingly, the molecular weight of the PAODA is preferably at least 400 g μmol. In various aspects, the PAODA has a molecular weight of at least 600 g/mol, or 800 g/mol, or 1,000 g μmol, or 1,200 g/mol, or 1,500 g/mol, or 2,000 g/mol.

Techniques to prepare PAODAs are well known in the art, and include reacting an initiator containing two hydroxyl groups with ethylene oxide and/or monosubstituted ethylene oxide followed by conversion of the resulting terminal hydroxyl groups to amines. Illustrative of the PAODA reactants employed herein are the JEFFAMINE™ brand of poly (alkyleneoxy)amines available from Huntsman Performance Chemicals (Houston, Tex., USA). These PAODAs are prepared from reactions of bifunctional initiators with ethylene oxide and propylene oxide followed by conversion of terminal hydroxyl groups to amines. Exemplary PAODAs are the XTJ and JEFFAMINE™ D-series poly(alkyleneoxy)diamines from Huntsman Chemicals (Salt Lake City, Utah, USA) which have approximate number average molecular weight between 150 and 4,000. As mentioned above, preferred PAODAs are those having an approximate molecular weight of at least about 400 g/mol, which are exemplified by JEFFAMINE™ D-400 and JEFFAMINE™ D-2000 PAODAs. As mentioned above, when the molecular weight of the PAODA is less than about 400 g/mol, the melting point of the corresponding polyamide becomes undesirably high for the polyamide to function as a gelling agent, and/or the mixture of reactants becomes too high-melting to readily form a molten mixture that may be reacted together to form a polyamide.

The relative amounts of CHDA and PAODA are important in preparing a polyamide-polyether copolymer having good gelling behavior and other properties. The reaction mixture that is prepared in order to form a polyamide-polyether of the present invention will have both diamine and diacid, and may have other optionally present reactants. The diamine may be a mixture of diamines, and independently, the diacid may be a mixture of diacids. In those instances where the diamine and/or the diacid is a mixture, the relative amounts of diamine in the mixture of diamine, and the relative amounts of diacid in the mixture of diacid, may be characterized in terms of equivalent(s) and/or equivalent percent, or may be characterized in terms of weight percent.

As used herein, the terms "equivalent(s)" and "equivalent percent" are intended to have their standard meanings as employed in the art. However, for additional clarity, it is noted that equivalents refer to the number of reactive groups present in a molar quantity of a molecule, such that a mole of a dicarboxylic acid (e.g., CHDA) has two equivalents of carboxylic acid, a mole of poly(alkyleneoxy)diamine has two equivalents of amine, and a mole of monoamine has one equivalent of amine.

For instance, the diamine component in the reaction mixture may be a blend of poly(alkyleneoxy)diamine and one or more co-diamines. In such a case, in various aspects of the invention, the poly(alkyleneoxy)diamine component of the diamine blend contributes at least 5 percent, or at least 10 percent, or at least 15 percent, or at least 20 percent, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95% of the amine equivalents from diamine present in the reaction mixture, with the remainder being co-diamine. Alternatively, the reaction mixture may be described in terms of the weight percent contributed by each component diamine of a blend of diamines, e.g., a blend of poly(alkyleneoxy)diamine and one or more co-diamines. In this case, in various aspects of the invention, the poly(alkyleneoxy)diamine component of the diamine blend contributes at least 5%, or at least 10%, or at least 15%, or at least 20%, or at least 25%, or at least 30%, or at least 35%, or at least 40%, or at least 45%, or at least 50%, of the total weight of all reactive components present in the reaction mixture.

In addition, or alternatively, the diacid component in the reaction mixture may be a blend of CHDA and one or more co-diacids. In such a case, in various aspects of the invention, the CHDA component of the diacid blend contributes at least 5 percent, or at least 10 percent, or at least 15 percent, or at least 20 percent, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95% of the acid equivalents from diacid present in the reaction mixture, with the remainder being co-diacid. Alternatively, the reaction mixture may be described in terms of the weight percent contributed by each component diacid of a blend of diacids, e.g., a blend of CHDA and one or more co-diacids. In this case, in various aspects of the invention, the CHDA component of the diacid blend contributes at least 5%, or at least 10%, or at least 15%, or at least 20%, or at least 25%, or at least 30%, or at least 35%, or at least 40%, or at least 45%, or at least 50%, of the total weight of all the reactive components charged to the reaction mixture.

In the case where the polyamide-polyether copolymer of the invention is prepared, at least in part, from a named diacid, e.g., CHDA or dimer acid, the reaction mixture used to prepare the copolymer may optionally contain co-diacid, i.e., diacid other than the named diacid. Among the possible reasons for addition of co-diacid to the copolymer-forming reaction mixture are (a) to reduce the cost of copolymer preparation, in the case where co-diacid is added to replace an equivalent amount of more expensive CHDA or dimer acid, (b) to modify the softening point of the copolymer, and (c) to modify the compatibility of the copolymer with a solvent.

As used herein, a co-diacid is a compound of formula HOOC—$R^7$—COOH where $R^7$ has a structure that does not afford the named diacid, e.g., does not afford CHDA or dimer acid when either is the named diacid. In one aspect, the polyamides of the present invention include $R^7$ groups having 2-32 carbons, which are referred to herein a co-diacid $R^7$ groups. Suitable co-diacids have a linear $C_{4-12}$ hydrocarbon group between the two carboxylic acid groups, and more preferably have a linear $C_{6-8}$ hydrocarbon group. Linear diacids suitable for the present invention include 1,6-hexanedioic acid (adipic acid), 1,7-heptanedioic acid (pimelic acid), 1,8-octanedioic acid (suberic acid), 1,9-nonanedioic acid (azelaic acid), 1,10-decanedioic acid (sebacic acid), 1,11-undecanedoic acid, 1,12-dodecanedioic acid (1,10-decanedicarboxylic acid), 1,13-tridecanedioic acid (brassylic acid) and 1,14-tetradecanedioic acid (1,12-dodecanedicarboxylic acid).

Another exemplary co-diacid for use in the present invention is the reaction product of acrylic or methacrylic acid (or the ester thereof, with a subsequent hydrolysis step to form an acid) and an unsaturated fatty acid. For example, a $C_{21}$ diacid of this type may be formed by reacting acrylic acid with a $C_{18}$ unsaturated fatty acid (e.g., oleic acid), where an ene-reaction presumably occurs between the reactants. An exemplary $C_{21}$ diacid is commercially available from Westvaco Corporation, Chemical Division, Charleston Heights, S.C., as their product number 1550.

Aromatic diacids may be used as the co-diacid. An "aromatic diacid" as used herein refers to a molecule having two carboxylic acid groups (—COOH) or reactive equivalents thereof (e.g., acid chloride (—COCl) or ester (—COOR)) and at least one aromatic ring ("Ar"). Phthalic acids, e.g., isophthalic acid and terephthalic acid, are exemplary aromatic co-diacids. The aromatic co-diacid may contain aliphatic carbons bonded to the aromatic ring(s), as in HOOC—$CH_2$—Ar—$CH_2$—COOH and the like. The aromatic co-diacid may contain two aromatic rings, which may be joined together through one or more carbon bonds, (e.g., biphenyl with carboxylic acid substitution) or which may be fused (e.g., naphthalene with carboxylic acid substitution).

In various aspects of the invention, the reaction mixture used to prepare the copolymer contains 0% co-diacid, or the co-diacid, when present, constitutes up to about 5%, or up to about 10%, or up to about 15%, or up to about 20%, or up to about 25%, or up to about 30%, or up to about 35%, or up to about 40%, or up to about 45%, or up to about 50%, or up to about 55%, or up to about 60%, or up to about 65%, or up to about 70% of the total weight of the reactants used to form the copolymer.

In one aspect of the invention, the co-diacid in combination with CHDA may be polymerized fatty acid, also referred to as dimer acid. Polymerized fatty acid is typically a mixture of structures, where individual dimer acids may be saturated, unsaturated, cyclic, acyclic, etc. Thus, a detailed characterization of the structure of dimer acid is not readily available. However, good discussions of fatty acid polymerization may be found in, e.g., U.S. Pat. No. 3,157,681 and *Naval Stores—Production, Chemistry and Utilization*, D. F. Zinkel and J. Russell (eds.), Pulp. Chem. Assoc. Inc., 1989, Chapter 23. Typical unsaturated fatty acids used to form polymerized fatty acid include oleic acid, linoleic acid, linolenic acid, etc. Tall oil fatty acid, which is a mixture containing long-chain unsaturated fatty acids obtained as a byproduct of the wood pulping process, is an exemplary source of polymerized fatty acid useful in the invention. Alternatively, polymerized fatty acid may be prepared by polymerization of unsaturated fatty acids from other sources, e.g., soybeans or canola. Thus, polymerized fatty acid typically contains 30-42 carbon atoms, and may be described as having the structure of dimer or trimer acid. Dimer acid is available commercially as, for example, UNIDYME™ and SYLVADYME™ dimer acids from Arizona Chemical (Jacksonville, Fla.), EMPOL™ dimer acid from Cognis (Ambler, Pa.); and PRIPOL™ dimer acid from Unichema North America (Chicago, Ill.).

Typically, upon the polymerization of fatty acid, both dimer acid and trimer acid are produced. This polymerization product may be subjected to distillation in order to remove all or most of the monomeric fatty acid species, and to fractionate the dimer and trimer acids. However, it is difficult and rather expensive to fractionate polymerized fatty acids to such an extent that they contain no trimer acid and/or no residual monomeric fatty acid. Accordingly, "dimer acid" as is commercially available often contains some trimer acid and/or monomeric acid, and the specification sheet for the dimer acid will typically list a trimer acid and/or monomeric acid content. Thus, the "dimer acid" that may be utilized to prepare copolymers of the present invention may contain some trimer acid and/or monomeric acid.

Preferably, the dimer acid contains less than about 25 wt % trimer acid, and in various aspects of the invention the dimer acid contains less than 20 wt %, or less than 15 wt %, or less than 10 wt %, or less than 5 wt % trimer acid. Also preferably, the dimer acid contains less than about 25 wt % residual monomeric acid, and in various aspects of the invention, the dimer acid contains less than 20 wt %, or less than 15 wt %, or less than 10 wt %, or less than 5 wt % monomeric fatty acid.

The ratio of monomeric fatty acid, dimer acid and trimer acid present in a polymerized fatty acid distillate can be determined by gas chromatography, according to methods well known in the art. Preferably, the amount of dimer acid present in the reaction mixture used to prepare the copolymer of the present invention is such that less than about 10% of the total acid equivalents in this mixture, or less than about 25% of the total weight of this mixture, comes from dimer acid.

In one aspect of the invention, the copolymer formed from a reaction mixture comprising 1,4-cyclohexane dicarboxylic acid (CHDA) and poly(alkyleneoxy)diamine is characterized in terms of the amine equivalents from diamine present in the mixture. In one embodiment, the poly(alkyleneoxy)diamine (PAODA) provides at least 20 percent of the amine equivalents from the diamine. In other embodiments, the PAODA provides at least 25 percent, or at least 30 percent, or at least 35 percent, or at least 40 percent, or at least 45 percent, or at least 50 percent, or at least 55 percent, or at least 60 percent, or at least 65 percent, or at least 70 percent, or at least 75 percent, or at least 80 percent, or at least 85 percent, or at least 90 percent, or at least 95 percent, or 100 percent of the amine equivalents from diamine present in the reaction mixture.

In another aspect of the invention, the copolymer formed from a reaction mixture comprising 1,4-cyclohexane dicarboxylic acid (CHDA) and poly(alkyleneoxy)diamine is characterized in terms of the amine equivalents from diamine that are present in the mixture and are contributed by short-chain aliphatic diamine having 2-6 carbons. As the term is used herein, a short-chain diamine refers to an aliphatic, cycloaliphatic, or aromatic moiety containing no more than 6 carbon atoms; "aliphatic" refers to a molecular moiety having a structure devoid of aromatic ring systems; "cycloaliphatic" refers to an aliphatic molecular moiety having a ring structure; and "aromatic" refers to a molecular moiety containing an aromatic ring structure such as, without limitation, phenyl or naphthyl. Exemplary short-chain diamines include ethylene diamine, 1,3-diaminopropane, 1,4-diaminobutane, 1,6-hexamethylene diamine, piperazine, 1,2-cyclohexane diamine, isophorone diamine, and m-xylene diamine. In one aspect, the short-chain diamine used to prepare a polyamide of the present invention is isophorone diamine or m-xylene diamine. As is discussed below, dimer diamine is not considered to be a short-chained diamine.

It has been discovered that the inclusion of even small amounts of CHDA in a polyamide-forming reaction mixture constrains the formulation to including only a select few short-chain diamines because most aliphatic diamines (e.g., ethylene diamine, hexamethylene diamine, piperazine) form intractable salts with CHDA upon mixing. While small amounts of diamines such as isophorone diamine or m-xylene diamine can be added to the reaction mixture without the formation of intractable salts, they also increase the softening point of the copolymer greatly.

Therefore, short-chain diamine is preferably up to about 10 amine equivalent percent, more preferably up to about 5 amine equivalent percent, and even more preferably up to about 2 amine equivalent percent, of the reaction mixture of the copolymer. In one embodiment, such short-chain diamines provide less than 10 percent of the amine equivalents from the diamine, while in another embodiment these short-chain diamines provide less than 5 percent of the amine equivalents from diamine, while in another embodiment these short-chain diamines provide none of the amine equivalents from diamine.

In another aspect of the invention, the copolymer formed from a reaction mixture comprising 1,4-cyclohexane dicarboxylic acid (CHDA) and poly(alkyleneoxy)diamine is characterized in terms of the acid equivalents from diacid present in the reaction mixture. In one embodiment, the CHDA provides at least 20 percent of the acid equivalents from the diacid. In related embodiments, the CHDA provides at least 2-5%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100% of the acid equivalents from diacid. When present, the remainder of the acid equivalents would be provided by co-diacid as described above.

In one embodiment, the reaction mixture used to form a copolymer of the present invention is characterized by acid equivalents from diacid, and polymerized fatty acid provides less than 10 percent of the acid equivalents from the diacid. In related embodiments, polymerized fatty acid provides less than 5 percent, or none of the acid equivalents from diacid.

In one aspect, the reaction mixture that forms the copolymer is about 1-50% 1,4-cyclohexane dicarboxylic acid (i.e., CHDA) by weight; more preferably the reaction mixture is about 2-35% 1,4-cyclohexane dicarboxylic acid by weight; and preferably the reaction mixture is about 5-25% 1,4-cyclohexane dicarboxylic acid by weight.

In one aspect, the polyamide of the invention is provided by reacting a major portion (>50% on an equivalent basis) of CHDA, an optional co-diacid such as sebacic acid, one or more poly(alkyleneoxy)diamines, a polymerized fatty diamine, or mixture of these diamines, a minor amount if any of an optional co-diamine, such as isophorone diamine, and an optional monoacid, monoalcohol, or monoamine to control molecular weight.

In one aspect of the invention, a polyamide-polyether block copolymer is provided that is prepared from a reaction mixture that includes CHDA, PAODA, and dimer diamine. Dimer diamine is derived from dimer acid as described herein, where the terminal —COOH groups of dimer acid are replaced with —NH$_2$ groups. It is, therefore, not a short-chained diamine, containing as it does approximately 36 carbon atoms, and does not form intractable salts in combination with CHDA. It is also, therefore, a component of the copolymers of the invention that contributes amorphous and fatty (i.e., non-polar) character to the copolymer. Dimer diamine may be prepared from dimer acid using synthesis schemes known to those of ordinary skill in the art (see, e.g., *March's Advanced Organic Chemistry: Reactions, Mechanisms, and Structure,* 5th edition, M. B. Smith and J. March, Wiley Interscience, New York, 2001). Dimer diamines are available commercially as, for example, products sold under the VERSAMINE® brand from Cognis Corporation (Cincinnati, Ohio).

When dimer diamine is a component along with CHDA in a polyamide forming reaction mixture, then in various aspects of the invention the dimer diamine is present at up to about 5%, or up to about 10%, or up to about 15%, or up to about 20%, or up to about 25%, or up to about 30%, or up to about 35%, or up to about 40%, or up to about 45%, or up to about 50%, or up to about 55%, or up to about 60% of the total weight of the reactants used to form the copolymer.

The following are some of the preferred embodiments of the present invention:

1) The copolymer has a softening point between 100° C. and 140° C. Copolymers having softening points within this range afford a good balance of good gelation properties and ease of dissolution with most solvents that are desirably gelled.

2) CHDA is the only diacid compound present in the reaction mixture. A formulation of this type will tend to provide relatively higher melting copolymer.

3) CHDA provides at least 45% of the acid equivalents attributed to the diacid compound(s). When the formulation contains less than this amount of CHDA, the copolymer has a lower softening point than is desired in most applications.

4) The diacid compound(s) comprise dimer acid. Dimer acid is desirably included in the reaction mixture because it typically lowers the cost of the formulation, lowers the softening point and provides the copolymer with good compatibility with less polar solvents.

5) Dimer acid provides less than 25% of the equivalents of the acid groups attributed to the diacid compound(s). When dimer acid provides more than about 25% of the equivalents of the acid groups attributed to the diacid compound(s), then the composition necessarily contains relatively less CHDA. Reducing the CHDA amount lowers the softening point below what is typically desirable for gelling most solvents.

6) The reaction mixture contains no monofunctional reactant. Since there is no terminating group used in this reaction mixture, the equivalents of acid from diacid should approximately equal (i.e., be within about 10% of) the equivalents of amine from diamine. The molecular weight of the polymer can, in this case, be adjusted by using an excess of one reactive group (acid or amine) over the other.

7) The reaction mixture contains a mono-carboxylic acid compound. The mono-carboxylic acid will function as a terminating group. Because the mono-carboxylic acid is used in a minor amount, the molecular weight of the mono-carboxylic acid does not greatly impact the properties of the copolymer. Nevertheless, for convenience, it is preferred that the monocarboxylic acid has a molecular weight of about 60-1,000 g/mol.

8) The reaction mixture contains a mono-amine compound. The mono-amine will function as a terminating group. Because the mono-amine is used in a minor amount, the molecular weight of the mono-amine does not greatly impact the properties of the copolymer. Nevertheless, for convenience, it is preferred that the mono-amine have a molecular weight of about 70-2,100 g/mol. Poly(alkyleneoxy) monoamine (PAOMA) is a suitable monoamine compound. However, when PAOMA is present in the mixture, the softening point of the copolymer tends to decrease. In order to raise the softening point of copolymer made from PAOMA, some of the PAODA may be replaced with co-diamine.

Exemplary monoamines include poly(alkyleneoxy) monoamines (i.e., PAOMAs), having the structure

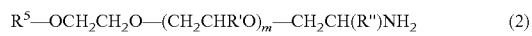

$$R^5\text{—OCH}_2\text{CH}_2\text{O—(CH}_2\text{CHR'O)}_m\text{—CH}_2\text{CH(R'')NH}_2 \qquad (2)$$

where R$^5$ is preferably an alkyl group; R' is preferably H, CH$_3$, or C$_2$H$_5$; and R" is preferably H or CH$_3$. Commercially available PAOMAs are typically prepared from ethylene oxide and/or propylene oxide and are available in varying ratios of propylene oxide to ethylene oxide-based residues. PAOMAs may be obtained from, e.g., Huntsman Chemicals (Houston, Tex., USA), sold under the XTJ and JEFFAMINE™ M-series trade names (e.g., M-2070).

9) The reaction mixture contains a mono-hydric compound. The mono-hydric compound will function as a terminating group. Because the mono-hydric compound is used in a minor amount, the molecular weight of the mono-hydric compound does not greatly impact the properties of the copolymer. Nevertheless, for convenience, it is preferred that the monohydric compound have a molecular weight of about 70-1,000 g/mol. Poly(alkyleneoxy)mono-hydric compound is a suitable mono-hydric compound. However, when poly(alkyleneoxy)mono-hydric compound is present in the mixture, the softening point of the copolymer tends to decrease. In order to raise the softening point of copolymer made from poly(alkyleneoxy)mono-hydric compound, some of the PAODA may be replaced with co-diamine.

10) The copolymer of claim 1 wherein the reaction mixture further comprises a dihydric compound. The dihydric compound may be used in lieu of an equal amount of diamine compound, on an equivalents basis. The dihydric compound, which may also be referred to as a diol, may be a short-chain diol, e.g., a compound of the formula HO—R—OH where R is a C$_2$-C$_8$ alkylene or cycloalkylene group (e.g., ethylene glycol, butylene glycol, cyclohexanedimethanol), or it may be a polyether diol, i.e., a compound of the formula HO—R—OH where R is —(CH$_2$CH$_2$O)$_n$CH$_2$CH$_2$— (n is 1 to about 500) and an ethylene group (i.e., CH$_2$CH$_2$) may be replaced in one or more occurrences with a propylene group (i.e., CH$_2$CH (CH$_3$)). Polyether diols are commercially available from many sources. A readily available polyether diol is known as PEG, i.e., polyethylene glycol, and is sold by Aldrich. When polyether diol is present in the reaction mixture, the polyether diol preferably contributes no more than 40 equivalent percent of the total of the diol and diamine reactants.

11) The reaction mixture further comprises a co-diacid. The diacid typically serves to lower the cost of the formulation and to reduce the softening point of the copolymer. Exemplary co-diacids include adipic acid, sebacic acid, azelaic acid, dodecanedioic acid, and 1,3-cyclohexane dicarboxylic acid.

12) PAODA is the only diamine compound present in the reaction mixture.

13) PAODA provides at least 20% of the amine equivalents attributed to the diamine compound(s) in the reaction mixture.

14) PAODA includes PAODA compounds having molecular weights between 400 and 5,000. PAODA compounds having molecular weight below about 400 tend to form intractable salts with the CHDA, and accordingly are either omitted from the reaction mixture, or are used in very small amounts. However, JEFFAMINE D-400, which has a molecular weight of about 440, does not cause an intractable salt-formation problem.

15) The diamine compound(s) present in the reaction mixture exclude diamines of the formula $H_2N-R^2-NH_2$ wherein $R^2$ is $C_2$-$C_6$ hydrocarbyl. Again, these very short chain diamines tend to form intractable salts with CHDA, and accordingly are preferably omitted from the reaction mixture. If present, they are preferably used in small amounts, so that they provide less than 10% of the amine equivalents attributed to diamine compound(s).

16) The copolymer has a weight average molecular weight of between 10,000 and 40,000, as measured using gel permeation chromatography with polystyrene as reference standards.

17) The copolymer has a weight average molecular weight in excess of 30,000, as measured using gel permeation chromatography with polystyrene as reference standards.

18) The diamine compound(s) comprise dimer diamine. Dimer diamine is a good addition to the reaction mixture in order to allow the mixture to have a high acid equivalents contributed to CHDA, but some fatty character to enhance gelation properties for less polar solvents.

19) The copolymer has low acid and amine numbers, where a low acid or amine number is less than 20, or less than 18, or less than 16, or less than 14, or less than 12, or less than 10, or less than 8, or less than 6, or less than 5, or less than 4, or less than 3, or less than 2. In exemplary embodiments, at least one of the acid or amine number of the copolymer is less than 20, or less than 18, or less than 16, or less than 14, or less than 12, or less than 10, or less than 8, or less than 6, or less than 5, or less than 4, or less than 3, or less than 2. In other exemplary embodiments, both of the acid and amine numbers of the copolymer are less than 20, or less than 18, or less than 16, or less than 14, or less than 12, or less than 10, or less than 8, or less than 6, or less than 5, or less than 4, or less than 3, or less than 2. For instance, the present invention provides copolymers that have an amine number of less than 10 and an acid number of less than 15.

In various aspects of the invention, any two or more of preferred features 1) through 19) may be combined in order to described a copolymer of the invention. For example, and for illustrative purposes only, it may be mentioned that feature 3) may be combined with feature 1), or feature 2), or feature 4), or feature 5), or feature 6), or feature 7), or feature 8), or feature 9), or feature 10), or feature 11), or feature 12), or feature 13), or feature 14), or feature 15), or feature 16), or feature 17), or feature 18), or feature 19). Likewise, feature 5) may be combined with feature 1), or feature 2), or feature 3), or feature 4), or feature 6), or feature 7), or feature 8), or feature 9), or feature 10), or feature 11), or feature 12), or feature 13), or feature 14), or feature 15), or feature 16), or feature 17), or feature 18), or feature 19). Likewise, feature 13) may be combined with feature 1), or feature 2), or feature 3), or feature 4), or feature 5), or feature 6), or feature 7), or feature 8), or feature 9), or feature 10), or feature 11), or feature 12), or feature 14), or feature 15), or feature 16), or feature 17), or feature 18), or feature 19). Likewise, feature 18) may be combined with feature 1), or feature 2), or feature 3), or feature 4), or feature 5), or feature 6), or feature 7), or feature 8), or feature 9), or feature 10), or feature 11), or feature 12), or feature 13), or feature 14), or feature 15), or feature 16), or feature 17), or feature 19).

More that two features as identified herein may be combined to characterize a copolymer of the present invention. For instance, in one aspect, the invention provides a copolymer having a softening point between 100° C. and 140° C.; where CHDA provides at least 45% of the acid equivalents attributed to diacid compound(s); dimer acid is present in the reaction mixture, however dimer acid provides less than 25% of the equivalents of acid groups attributed to the diacid compound(s); and PAODA provides at least 20% of the amine equivalents attributed to the diamine compound(s).

The copolymers of the present invention contain at least one polyether (i.e., polyalkyleneoxy) block, and at least one polyamide block (where the polyamide block may, but does not necessarily, include polyether groups). The polyether block is preferably introduced into the copolymer by way of a reactive polyether, i.e., a polyether having one or two reactive terminal group such as an amine, an acid or an alcohol. The presence of both polyether and polyamide blocks has been discovered to be an extremely efficacious combination for the copolymer to function as a gellant. In general, in one aspect of the invention, it is preferred that polyether groups (also referred to as polyalkyleneoxy (PAO) groups) constitute about 30-60 wt % of the weight of the copolymer. In other words, the reactants that introduce polyether groups into the copolymer constitute, in one aspect of the invention, 30-60% of the total weight of the reactants. In one aspect, the reactants the are used to introduce polyether groups into the copolymer are selected from PAO-MA (monoamine terminated polyether), PAO-DA (diamine terminated polyether, i.e., each of the two termini of the PAO is an amine group), PAO-COOH (carboxylic acid terminated polyether), PAO-OH (hydroxyl terminated polyether), HO-PAO-OH (dihydroxyl terminated polyether, i.e., each of the two termini of the PAO is a hydroxyl group). In a related aspect, the polyether groups constitute about 40-50 wt % of the total weight of the reactants used to form the copolymer. In a preferred embodiment, the PAO groups are introduced into the copolymer via monoamine and diamine-terminated polyalkyleneoxy groups. In another preferred embodiment, at least some PAO-DA is used to introduce polyether groups into the copolymer. In another preferred embodiment, the PANDA has a molecular weight of 1,000-3,000, more preferably 1,500 to 2,500.

As mentioned above, mono-carboxylic acid may be present as one of the components of the reaction mixture. In such a case, the copolymer of the invention may be described as including a macromolecule of formula (3):

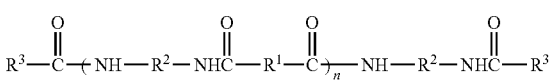

(3)

wherein, in at least one occurrence, $R^1$ is a $C_6$ carbocyclic group derived from CHDA; $R^2$ is a polyalkyleneoxide moiety derived from PAODA; $R^3$ is a hydrocarbon group having at least 2 carbons; and n is an integer of at least 11. By specifying that n is an integer of at least 11, the present invention is directed to relatively high molecular weight copolymers, e.g., copolymers having a macromolecule of formula (1) with a molecular weight of greater than 30,000.

As mentioned above, mono-amine may be present as one of the components of the reaction mixture. In such a case, the copolymer of the invention may be described as including a macromolecule of formula (4):

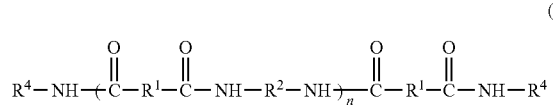

wherein, in at least one occurrence, $R^1$ is a $C_6$ carbocyclic group derived from CHDA; $R^2$ is a polyalkyleneoxide moiety derived from PAODA; $R^4$ is selected from a hydrocarbon group having at least 4 carbons and a polyalkyleneoxide moiety having a formula weight of at least 100; and n is an integer of at least 11. By specifying that n is an integer of at least 11, the present invention is directed to relatively high molecular weight copolymers, e.g., copolymers having a macromolecule of formula (1) with a molecular weight of greater than 30,000.

As mentioned above, mono-hydric compound (also referred to herein as monoalcohol) may be present as one of the components of the reaction mixture. In such a case, the copolymer of the invention may be described as including a macromolecule of formula (5):

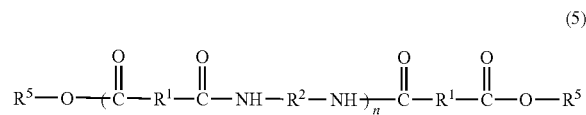

wherein, in at least one occurrence, $R^1$ is a $C_6$ carbocyclic group derived from CHDA; $R^2$ is a polyalkyleneoxide moiety derived from PAODA; $R^5$ is selected from a hydrocarbon group having at least 4 carbons and a polyalkyleneoxide moiety having a formula weight of at least 100; and n is an integer of at least 11. By specifying that n is an integer of at least 11, the present invention is directed to relatively high molecular weight copolymers, e.g., copolymers having a macromolecule of formula (1) with a molecular weight of greater than 30,000.

In another aspect of the invention, a polyamide-polyether block copolymer is provided that is necessarily made from dimer acid and poly(alkyleneoxy)diamine (or reactive equivalents thereof), both as described above, but is not necessarily made from CHDA. In this aspect, the present invention provides a copolymer formed from a reaction mixture comprising dimer acid, poly(alkyleneoxy)diamine, and short-chain aliphatic diamine (SDA). In this aspect, the reaction mixture will include some amount ("x grams" for convenience) of poly(alkyleneoxy)diamine and some amount ("y grams" for convenience) of short-chain aliphatic diamine. The PAODA should be present in major weight proportion compared to the sum of PAODA and SDA, and more preferably, x/(x+y) is about 0.8-0.98. In addition, the PAODA should contribute a significant amount of the weight of the total reactants. For example, if the reaction mixture has a total weight ("z grams" for convenience), then the PAODA contributes at least 25% of that weight, i.e., x/z>0.25. In related aspects, x/z is at least 0.3, or at least 0.35, or at least 0.4, or at least 0.45, or at least 0.5. In addition, the reaction mixture contains either no co-diacid, or comprises a minor amount of co-diacid, wherein, if the reaction mixture comprises a minor amount of co-diacid, then acid equivalents from co-diacid contribute less than 25% of the total acid equivalents from dimer acid and co-diacid. Although it does tend to increase the copolymer softening point, co-diacid is not very desirable in this formulation because its presence tends to increase the crystallinity of the copolymer, and thereby decrease the good gelation properties of the copolymer.

The discussion of PAODA as set forth above for the CHDA-containing copolymers apply equally to these PAODA-containing copolymers that do not necessarily contain CHDA, For example, in one aspect, the copolymer has a softening point is between 100° C. and 140° C. In another aspect, dimer acid is the only diacid compound present in the reaction mixture. In another aspect wherein co-diacid is present in the reaction mixture, the co-diacid contributes less than 10% of the total acid equivalents from dimer acid and co-diacid. In another aspect, PAODA and SDA together constitute at least 95 wt % of the diamine compounds present in the reaction mixture. In another aspect, the reaction mixture includes poly(alkyleneoxy)diamine having a molecular weight of at least 400 g/mol. In another aspect, co-diacid is not present in the reaction mixture. In other aspects, PAODA is about 80-98% of the weight of poly(alkyleneoxy)diamine plus short-chain aliphatic diamine; and poly(alkyleneoxy) diamine residues are at least 20%, or at least 30%, or at least 40%, or at least 50% of the total weight of the copolymer.

As mentioned briefly above, in any of the polyamide-polyether copolymers of the present invention, the reaction mixture used to form the copolymer may contain some monofunctional reactant that will serve primarily to adjust the molecular weight of the copolymer and reduce the acid and amine number of the copolymer. Such monofunctional reactants are, in one embodiment, selected from monocarboxylic acid, monoamine and monoalcohol. The term "monocarboxylic acid" refers to an organic molecule having a single carboxylic acid group, i.e., a single group of the structure —COOH. The term "monoamine" refers to an organic molecule having a single amine group, where the amine group may be a primary or secondary amine. The term "monoalcohol" refers to an organic molecule having a single hydroxyl (—OH) group.

An exemplary monofunctional reactant is a monocarboxylic acid having the structure R—COOH, wherein R is polyether, alkyl, alkenyl, or alkynyl. Another exemplary monofunctional reactant is a monoamine of the structure R—$NH_2$. As used herein, "alkyl" refers to a hydrocarbyl monovalent radical containing only single bonds, while "alkenyl" and "alkynyl" are hydrocarbyl monovalent radicals containing at least one C=C double bond and one C≡C triple bond, respectively. The presence of monocarboxylic acid or monoamine in the reaction mixture serves to inhibit further elongation of the resulting polyamide chains, thereby preventing the molecular weight of the copolymer from becoming too large.

Exemplary monocarboxylic acids for use in this invention include, without limitation, short-chain aliphatic carboxylic acids, saturated fatty acids (e.g., wherein R is alkyl) and unsaturated fatty acids (e.g., wherein R is alkenyl or alkynyl). Specific exemplary short-chain aliphatic carboxylic acids include, without limitation, acetic, propionic, and butanoic acids, while exemplary saturated fatty acids include, without limitation, valeric, caproic, caprylic, lauric, myristic, palmitic, stearic, isostearic, arachidic, behenic, lignoceric, cerotic, and montanic acids, and exemplary unsaturated fatty acids include, without limitation, caproleic, palmitoleic, oleic, vaccenic, eladic, brassidic, erucic, and nervonic acids. In various additional aspects of the invention, the monocarboxylic acid is up to about 20 weight percent, more preferably up to about 10 weight percent, and even more preferably up to about 5 weight percent, of the reaction mixture used to form a copolymer of the present invention.

Exemplary monoalcohols are the monoamines as described above wherein the terminal amine group is replaced with a hydroxyl group, and the monocarboxylic acid groups as described above wherein the terminal carboxylic acid group has been reduced to a primary alcohol group.

When monofunctional reactant is present in a polyamide-forming reaction mixture, the amount of monofunctional reactant may be selected in view of the preferred molecular weight of the product polyamide. The molecular weight decreases as the amount of monofunctional reactant in the reaction mixture increases. In various aspects, the monofunctional reactants contributes, less than 5%, or less than 10%, or less than 15%, or less than 20%, or less than 25%, or less than 30%, or less than 40%, or less than 50% of the total weight of the polyamide-forming reactants in the polyamide-forming reaction mixture. In one aspect, the monofunctional reactant is monoamine, while in another aspect the monofunctional reactant is monoacid, while in another aspect the monofunctional reactant is monocarboxylic acid. In still another aspect, the reaction mixture includes polyether monoamine.

In the polyamide-polyether block copolymers of the present invention, the inclusion of a significant level of PAODA in the polyamide-forming reaction mixture, or in other words, the inclusion of polyether functionality located between two amide groups, allows these copolymers to form clear solutions and/or clear gels in a wide range of organic liquids. It is desirable that the reaction mixture used to form the copolymer does not contain too little PAODA. Too little PAODA results in a hard copolymer having a medium to high softening point, but with poor ability to gel an organic liquid. In the extreme case, the copolymer simply is incompatible with the organic liquid, and will not dissolve in the organic liquid when heated. Although it is generally preferred that a copolymer contain a high level of PAODA, for gelation of some organic liquids a copolymer may contain too much PAODA and have little or no gelation ability. In the extreme case here, the copolymer dissolves very readily in the organic liquid, but the polyamide molecules are so solvated that a gel cannot set up. For optimal gelation performance properties according to the present invention, the copolymer is prepared from a reaction mixture that preferably has about 25-80 wt %, more preferably 30-60 wt % PAODA.

As an exemplary preparation scheme for the copolymers of the present invention, the reaction components are charged to a reaction flask fitted with a thermocouple probe, nitrogen inlet, and magnetic stir bar. The flask has a vapor outlet leading to a moisture trap and exiting to the back of a fume hood. The flask is then covered with aluminum foil or an insulating fiberglass pad, and the reaction mixture is heated to about 220° C. under a gentle stream of nitrogen as rapidly as occasional foaming allows. Nitrogen flow is then increased to aid in water removal, and the reaction mixture is held at this temperature for approximately 6 hours. In most cases, these conditions result in a copolymer having satisfactory acid and amine numbers (typically each less than 15). The reaction mixture is then cooled to ambient temperature and discharged, providing a copolymer suitable for use as a liquid gellant.

The one-pot method as described above is probably the simplest method to prepare small amounts of a copolymer of the present invention. However, especially when more than two reactants are used to prepare the copolymer, or for preparing very large amounts of co-polymer, these reactants may be metered into the reaction vessel rather than being charged all at once in the beginning of the reaction. The reaction vessel may be jacketed to allow heating by hot oil. The vessel may also be equipped with a motor-driven paddle-blade stirrer, and is preferably configured so that it is capable of being evacuated to a low pressure to assist in water removal.

The polyamide-polyether copolymers of the present invention are particularly useful as gelling agents, also known as rheological modifiers. That is, the combination of polyamide-polyether and a liquid results in the formation of a gel. In a typical assay for gelation ability of the polyamide-polyether copolymers of the present invention, about 0.6 grams of copolymer and about 3.4 grams of liquid are charged to a test tube before being capped with aluminum foil. The test tube is placed in an oven at about 115° C. and incubated for about 1 hour. The tube is then removed, agitated while still hot on a vortex stirrer briefly to ensure good copolymer contact with the solvent, and returned to the oven. After incubation for about 1 additional hour, the tube is removed and allowed to cool to ambient temperature. Tubes containing copolymers not fully dissolved after this treatment are placed in an oven about 10° C. warmer, and the procedure is repeated until the copolymer is fully dissolved. The sample is then removed from the oven and allowed to cool. The cooled copolymer solution is then rated for gel quality as follows:

"Gel": solution does not flow or slump when inverted and shaken strongly;

"Jelly": solution slumps, or cracks when shaken;

"Paste": mixture is soft, hazy to very cloudy and inhomogeneous, slumps or flows when inverted;

"2-Phase": dissolves when hot but separates upon cooling into cloudy/hazy phases;

"Incompatible": copolymer does not dissolve when hot, forms a separated solid top layer;

"Soluble": solution is clear and fluid.

The clarity of the copolymer solutions may be characterized as follows:

"Crystal clear", where this term is self-explanatory;

"Hazy": solution is not clear but print is legible when viewed through the solution, where modifiers include "very," "slight," and "very slight;" and "Cloudy": cannot see through the solution at all, where modifiers include "very," "slight," and "very slight."

In one aspect of the present invention, the polyamide-polyether copolymer is a gelling agent for ethyl lactate, i.e., a gel is formed when the copolymer and ethyl lactate are combined as described above. In other words, following the protocol outlined above, the resulting mixture at room temperature is a "gel". In another aspect, the polyamide-polyether copolymer is a gelling agent for dibutyl adipate.

Thus, the present invention provides a composition comprising a polyamide-polyether copolymer as described herein, and a compound or mixture of compounds, where the compound or mixture is a liquid at room temperature in neat form. This composition will typically be fluid at elevated temperature, and will typically be a gel at room temperature. In one aspect, the compound has a functional group, i.e., the compound is not simply a hydrocarbon. In various aspects, that functional group is ester, or an ether, or a halogen, or a carbonate, or a sulfoxide. Mixtures that can be gelled may contain two, three or many of these compounds and functional groups. Specific compounds and class of compounds that may be gelled by the polyamide-polyether copolymers of the invention are described next, however, it should be appreciated that the copolymers described herein are capable of gelling a wide range of organic liquids and blends of organic liquids.

In one aspect, the organic liquids suitable for gelation by the polyamide polyether copolymers of the present invention are polar in nature. As used herein, "organic" refers to a chemical component containing at least one carbon atom. A polar liquid is one exhibiting dominant structural moieties of induced positive and negative charge (e.g., methanol), while a nonpolar liquid is one wherein the molecular structure is devoid of regions having induced positive and negative charge (e.g., carbon tetrachloride). Exemplary organic liquids suitable for gelation by the copolymers of the present invention include, without limitation, alcohols such as ethanol and propylene glycol; stripping solvents such as dimethyl sulfoxide (i.e., DMSO), N-methylpyrrolidinone (i.e., NMP), various terpenes and various ketones; epoxies such as EPON™ 828 (Resolution Performance Products, Houston, Tex.); and polymerizable monomers including alkyl acrylates, polyacrylates and styrene resin solutions.

Ester-containing compounds are another class of liquids suitable for gelation by the copolymers of the present invention. An ester-containing compound will include the structural formula —C(=O)—O—, and preferably includes the structural formula —C(=O)—O—$R^6$ where $R^6$ is selected from $C_{1-22}$ hydrocarbyl groups. Such esters may be monofunctional esters (i.e., have a single ester moiety) or may be polyfunctional (i.e., have more than one ester group). Suitable esters include, but are not limited to, the reaction products of $C_{1-24}$ monoalcohols with $C_{1-22}$ monocarboxylic acids, where the carbon atoms may be arranged in a linear, branched and/or cyclic fashion, and unsaturation may optionally be present between carbon atoms. Preferably, the ester has at least about 18 carbon atoms. Examples include, but are not limited to, fatty acid esters such as methyl oleate, methyl linoleate and mixtures containing methyl oleate and methyl linoleate such as methyl soyate or other vegetable oil methyl esters, isopropyl isostearate, n-propyl myristate, isopropyl myristate, n-propyl palmitate and isopropyl palmitate. Other suitable esters include alkyl benzoates such as FINNSOLV™ EB and FINNSOL™ TN, alkyl salicylates such as methyl salicylate (also known as oil of wintergreen), phthalates such as dioctyl phthalate, glycerol and propylene glycol esters of fatty acids, such as the so-called polyglycerol fatty acid esters (e.g., esters suitable for use in cosmetic formulations, such as glyceryl monostearate) and triglycerides.

Poly(alkyleneoxy)ethers are another class of liquids suitable for gelation by the copolymers of the present invention. Suitable poly(alkyleneoxy)ethers include, without limitation, polyethylene glycol; polypropylene glycol; DOWANOL™ EPH ethylene glycol monophenyl ether and DOWANOL™ DPM dipropylene glycol monomethyl ether (available from Dow Chemical, Midland, Mich. USA); surfactants such as TERGITOL™ NP-4 and TRITON™ X-100 (both available from Union Carbide), SURFONIC™ 40, SURFONIC™ DNP-100, and SURFONIC™ N-60 (all available from Huntsman Chemicals, Houston, Tex.), and polyoxyethylene monolaurate (marketed as GLYCOSPERSE™ L20 by Lonza, Inc., Fair Lawn, N.J.). Especially suitable are surfactants useful in preparing cosmetics and having an HLB number greater than 4 and less than 20, preferably 6-16. Such surfactants are well known in the art.

In further aspects, the present invention provides various articles of manufacture that include a polyamide-polyether copolymer as described herein. For example, one aspect of the present invention provides a gelled article that includes an active ingredient. In one embodiment, this aspect of the invention provides for a gelled composition that emits or otherwise makes available to its surrounding environment one or more active ingredients of the gelled composition. Illustrative active ingredients are fragrance materials, insecticides, insect-repellent and bioactive ingredients. In another embodiment, the active ingredient may be active while remaining within the gel. Examples of such active ingredients include, without limitation, colorant and sunscreen. Thus, this aspect of the invention provides for air fresheners, fragrance sticks, fragranced soft gels, insect repellents, insecticides, color-delivery compositions, sunscreens and other dermatological compositions, and the like.

In one aspect, the active ingredient is somewhat volatile in order that it may be emitted and released from the gel. However, the active ingredient may become volatile under the conditions of use for the article. For example, an active ingredient may be emitted in the sense that it migrates to the surface of the gel and then comes into contact with the environment. Articles which emit an active ingredient into the environment in order to have the desired effect may, for convenience, be collectively referred to herein as controlled release compositions.

In one aspect, the active ingredient is a fragrance material. Suitable fragrance materials include fine perfumes and commodity fragrance materials. Because almost all fragrance materials are at least moderately polar organic liquids, having functional groups such as alcohols, ethers, ketones and esters, a large number of suitable fragrance materials known to one of ordinary skill in the art may be gelled by the copolymers of the present invention. The fragrance-containing compositions of the present invention provide for controlling the shape and release of fragrance, i.e., providing the fragrance in the form of a solid gel with a steady release of fragrance which lasts for a long time. When the fragrance material is a fine fragrance, the gelled composition is preferably in the form of a stick, which can be rubbed onto a surface to provide a layer of fragrance-releasing material. Such a composition will be referred to herein as a fragrance stick. Alternatively, the gelled composition may be a "soft gel" by which is meant a composition of gelatin-like consistency. A soft gel does not typically hold its structure under stress, and thus is preferably contained within a jar or the like. A soft gel may be applied to the skin or other surface by immersing a finger into the gel and then rubbing the residue from the finger onto another area of the skin. The term "fine fragrance" generally refers to fragrances that are used in fine (e.g., expensive) perfumes. Alternatively, the gelled composition may be an attractively or usefully shaped object that holds its shape or shrinks slightly while the fragrance is released. Such as composition will be referred to herein as an air freshener since it is useful in fragrancing or "freshening" a room, closet, automobile or other enclosed space.

In a typical fragranced stick, air freshener or soft gel of the invention, the fine fragrance is present at a concentration within the range of about 1-70 wt. % of the composition, and preferably constitutes about 2-25 wt. % of the composition. The copolymer is typically present at a concentration within the range of about 5-50 wt. % of the composition, and is preferably present within the range of about 10-20 wt. %. Greater or lesser amounts of these ingredients may be present, depending on the desired consistency of the stick and the compatibility of the fragrance with the copolymer. In general, the gel structure becomes firmer as the concentration of polyamide-polyether block copolymer increases in the fragrance stick, air freshener, or soft gel and all of these can adopt a "stick" type consistency, which refers to a very firm, even free-standing, gel. The combination of polyamide-polyether block copolymer and fragrance can afford a clear or transparent structure. Such a transparent structure may increase the aesthetic appeal and application areas of the stick, freshener and gel in the marketplace.

The above articles of this invention are prepared from components that include a polyamide-polyether block copolymer as described herein. A typical inventive air freshener, fragrance stick or fragrance gel contains polyamide-polyether copolymer in a concentration range of about 5-60 wt %, and fragrance in a concentration range of about 1-70, where these weight percent values are based on the total weight of the article. The amounts of polyamide-polyether copolymer and fragrance present in the air freshener can be varied outside these typical ranges, and still provide a useful product. The precise amounts of polyamide-polyether copolymer and fragrance to be used in preparing an article will depend on the qualities of the particular polyamide-polyether copolymer. Typically, a high fragrance content is desirable in, for example, an air freshener because such an air freshener may potentially have a longer useful lifetime. It is usually advantageous to include a colorant, typically a dye, in the article to present an attractive appearance. Colorant levels are typically low on a weight basis, in the range of 0.05% to 2%.

Another active ingredient that may be incorporated into a gel of the invention is an anti-insect chemical. The term "anti-insect chemical" is intended to encompass materials that are toxic, repugnant or attractive to an insect. The gel containing the anti-insect chemical preferably has the consistency of a stick, or at least a firm gel, and will be referred to herein for convenience as an insect stick. The insect stick of the invention may be used to impart an anti-insect residue, in the form of a thin film, to a surface. Such a residue may be placed onto the surface of a cupboard, for example, in order to kill and/or repel insects from the cupboard. Alternatively, the thin film may be applied to the skin, to repel insects such as mosquitoes from the skin.

In a typical insect stick of the invention, the polyamide-polyether copolymer content will range from about 5-60 wt. % of the stick, and preferably ranges from about 10-50 wt. %. The content of anti-insect chemical will typically range from 0.1-30 wt. %. The amount of anti-insect chemical to be used in the insect stick will depend on the potency of the anti-insect chemical, as well as its compatibility with the polyamide-polyether copolymer. Suitable anti-insect chemicals include boric acid, synthetic pyrethroid, D-empenthrin and DEET. Other anti-insect chemicals as known in the art may also or alternatively be incorporated into the gel of the invention. One such chemical is referred to as a pheromone. Such a material can influence the behavior of an insect and thus be used to control its population. A pheromone can, for example, attract an insect to an area where it causes no damage or can be trapped.

The following is a list of chemicals that may be included in a formulation containing polyamide-polyether copolymer of the present invention, where release of the chemical into the environment will affect the behavior of insects: E or Z-13-octadecenyl acetate, E or Z-11-hexadecenal; E or Z-9-hexadecenal; hexadecanal; E or Z-11 hexadecenyl acetate; E or Z-9-hexadecenyl acetate; E or Z-11-tetradecenal; E or Z-9-tetradecenal; tetradecanal; E or Z-11-tetradecenyl acetate; E or Z-9-tetradecenyl acetate; E or Z-7-tetradecenyl acetate; E or Z-5-tetradecenyl acetate; E or Z-4-tridecenyl acetate; E or Z-9-dodecenyl acetate; E or Z-8 dodecenyl acetate; E or Z-5-dodecenyl acetate; dodecenyl acetate; 11-dodecenyl acetate; dodecyl acetate; E or Z-7-decenyl acetate; E or Z-5-decenyl acetate; E or Z-3-decenyl acetate; Z or E, Z or E 3,13-octadecadienyl acetate; Z or E, Z or E 2,13-octadecdienyl acetate; Z, Z or E-7,11-hexadecadienyl acetate; Z, E 9,12-tetradecadienyl acetate; E, E-8,10-dodecadienyl acetate; Z, E 6,8-heneicosadien-11-one; E, E 7,9-heneicosadien-11-one; Z-6-henicosen-11-one; 7,8-epoxy-2-methyloctadecane; 2-methyl-7-octadecene, 7,8-epoxyoctadecane, Z, Z, Z-1,3,6, 9-nonadecatetraene; 5,11-dimethylheptadecane; 2,5-dimethylheptadecane; 6-ethyl-2,3-dihydro-2-methyl-4H-pyran-4-one; methyl jasmonate; alpha-pinene; beta-pinene; terpinolene; limonene; 3-carene; p-cymene; heptane; ethyl crotonate; myrcene; camphene; camphor; cineol; alpha-cubebene; allyl anisole; undecanal; nonanal; heptanal; E-2-hexenal; E-3-hexenal; hexanal; verbenene; verbenone; verbenol; 3-methyl-2-cyclohexenone; 3-methyl-cyclohexenone; frontalin; exo and endo brevicomin; lineatin; multistriatin; chalcogran; 7-methyl-1,6-dioxaspiro(4.5-decane, 4,8-dimethyl-4(E),8(E)-decadienolide; 11-methyl-3(Z)-undecenolide; Z-3-dodecen-11-olide; Z,Z-3,6-dodecen-11-olide; Z-5-tetradecen-13-olide; Z,Z-5,8-tetradecen-13-olide; Z-14-methyl-8-hexadecenal; 4,8-dimethyldecanal; gamma-caprolactone; hexyl acetate; E-2-hexenyl acetate; butyl-2-methylbutanoate; propylhexanoate; hexylpropanoate; butylhexanoate; hexylbutanoate; butyl butyrate; E-crotylbutyrate; Z-9-tricosene; methyl eugenol; alpha-ionone; 4-(p-hydroxyphenyl)-2-butanone acetate; E-beta-famasene; nepetalactone; 3-methyl-6-isopropenyl-9-decenyl acetate; Z-3-methyl-6-isopropenyl-3,9-decadienyl acetate; E or Z-3, 7-dimethyl-2,7-octadecadienyl propionate; 2,6-dimethyl-1, 5-heptadien-3-ol acetate; Z-2,2-dimethyl-3-isopropenylcyclobutanemethanol acetate; E-6-isopropyl-3,9-dimethyl-5,8-decadienyl acetate; Z-5-(1-decenyl)dihydro-2(3H)-furanone; 2-phenethylpropionate; 3-methylene-7-methyl-7-octenyl propionate; 3,11-dimethyl-2-nonacosanone; 8-methylene-5-(1-methylethyl)spiro(11-oxabicyclo)8.1.0-undecene-2,2-oxiran-3-one; 2-propylthietane; 3-propyl-1,2-dithiolane; 3,3-dimethyl-1,2-dithiolane; 2,2-dimethylthietane; E or Z-2,4,5-trimethylthiazoline; 2-sec-butyl-2-thiazoline; and isopentenyl methyl sulfide. Specific pheromones include the following: 8-methyl-2-decyl-propionate; 14-methyl-1-octadecene; 9-tricosense; tridecenyl acetate; dodecyl acetate; dodecenyl acetate; tetradecenyl acetate; tetradecadienyl acetate; hexadecenyl acetate; hexadecadienyl acetate; hexadecatrienyl acetate; octadecenyl acetate; dodecadienyl acetate; octadecadienyl acetate; Z,E-9, 12-tetradecadiene-1-ol; hexadecenal; octadecenal; acetophenone; amyl acetate; isoamyl acetate; vanillin; or a flavorant selected from coffee, fennel and cinnamon flavor.

Other active ingredients that may be included in an article of manufacture of the present invention functions primarily while being maintained within the gel. Examples of such active ingredients include colorant and sunscreen. When the active ingredient is a colorant, then the product may be used to impart desired coloration to a surface, and/or to hide underlying and undesirable coloration. The active agent may be a sunscreen, where suitable sunscreens include, without limitation, PABA, ethylhexyl p-methoxycinnamate, oxybenzone, 2-ethylhexyl salicylate, octylsalicylate, and metal oxide such as zinc oxide and titanium oxide. The zinc oxide and titanium oxide scatter light so that less light hits the underlying skin.

Another active ingredient that may be included in an article of manufacture of the present invention is a bioactive compound. As used herein, a bioactive compound acts on a biological system to produce a desirable result. In a preferred embodiment, the bioactive compound may be applied to the skin of a person, to have a desirable effect on the person. The gel of the present invention thus can serve as a carrier for delivering the bioactive compound to the biological system, and/or as a means to hold the bioactive compound at a site to which it has been delivered, and/or as a repository of bioactive compound which provides for the controlled release of the bioactive compound to the system. The amount of this type of active ingredient to incorporate into the composition will depend on the desired effect, and such an amount can be readily determined by one of ordinary skill in the art without undue experimentation. At a minimum, the amount should be an effective amount. Typically, 0.1-25 wt. %, and more typically 0.5-10 wt % of the active ingredient is sufficient, where the wt. % value is based on the entire weight of the composition.

The bioactive compound may be cosmetic/dermatological agent that produces a desirable result on the host when applied to the host's skin. Exemplary desirable results include, without limitation, anti-fungal activity, hemorrhoid treatment, anti-itching treatment, wart removal or reduction, antibiotic activity, anti-wrinkling, and analgesic effects. Suitable cosmetic/dermatological agents include, without limitation, acetylsalicylic acid, acyclovir, 6-[3-(1-adamantyl)-4-methoxyphenyl]-2-naphthoic acid, amphotericin B, ascorbic acid, benzoyl peroxide, betamethasone valerate, chloroxylenol, citric acid, clindamycin phosphate, clobetasol propionate, clotrimazole, cyproheptadine, diclofenac, diphenylhydramine hydrochloride, econazole, erythromycin, estradiol, glycolic acid, glycyrrhetinic acid, hydrocortisone, hydroquinone, ibuprofen, ketoconazole, kojic acid, lactic acid, lidocaine hydrochloride, metronidazole, miconazole, miconazole nitrate, octopirox, 5-n-octanoylsalicylic acid, paracetamol, pramoxine hydrochloride, progesterone, retinoic acid, retinol, salicylic acid, superoxide dismutases, terbinafine, thenaldine, tocopherol, tolnaftate, trimeprazine, 1,8,10-tripropionyl-9-anthrone, undecylenate, and vitamin D.

The bioactive agent may be function as a topical analgesic, where exemplary topical analgesics include, without limitation, camphor, capsicin, menthol, methyl salicylate, and trolamine salicylate. The bioactive agent may function as an anti-fungal agent, where exemplary anti-fungal agents include, without limitation, clotrimazole, miconazole nitrate, tolnaftate, and undecylenate. Exemplary anti-itching agents include, without limitation, pramoxine hydrochloride and diphenylhydramine hydrochloride. An exemplary anti-wart compound for including in a gel of the invention is salicylic acid. An exemplary hemorrhoid treating compound for including in a gel of the invention is hydrocortisone. An exemplary antibiotic compound for including in a gel of the invention is chloroxylenol.

The bioactive agent may function as a wound-healing aid for preventing and reducing injury to mammalian cells and increasing the resuscitation rate of injured mammalian cells, where an exemplary wound-healing aid is a combination of (a) pyruvic acid and pharmaceutically acceptable salts thereof, and (b) a mixture of saturated and unsaturated fatty acids required for the repair of cellular membranes and resuscitation of mammalian cells. The bioactive agent may be an antioxidant, which inhibits oxidation or suppression reactions promoted by oxygen or peroxides, where exemplary antioxidants include, without limitation, vitamin A, vitamin E, and derivatives thereof. The bioactive agent may function as an anti-acne agent. Exemplary anti-acne agents include, without limitation, benzoyl peroxide and vitamin A acid.

The amount of bioactive ingredient to incorporate into the gel of the invention will depend upon the efficacy of the bioactive ingredient and the desired effect. This amount can be determined by one of ordinary skill in the art without undue experimentation. At a minimum, the amount should be an effective amount. Typically, 0.1 wt % to 25 wt %, and more typically 0.2 wt % to 10 wt % of bioactive ingredient is sufficient.

The article of manufacture containing a polyamide-polyether copolymer of the present invention may be a personal care product, where exemplary personal care products include, without limitation, eye make-up (mascara, shadow), finger nail polish, facial scrubs, lipstick, foundation make-up, costume makeup, as well as baby oil, make-up removers, bath oil, skin moisturizers, sun care products, lip balm, waterless hand cleaner, medicated ointments, ethnic hair care products, perfume, cologne, and suppositories.

In addition, the polyamide-polyether copolymer-containing gels of the present invention may be used in household products such as automobile wax/polish, candles, furniture polish, metal cleaners/polishes, household cleaners, paint strippers and insecticide carriers.

The polyamide-polyether copolymer-containing gels of the present invention may also be used in industrial products such as fuels (sterno, lighter, fire-starters), toilet bowl rings, lubricants/greases, wire rope lubricant, joint and cable fillers, soldering flux, buffing compounds, crayons and markers, modeling clay, rust preventatives, printing inks, paints, protective/removable coatings, and jet inks.

Formulations to prepare such materials are well known in the art. For example, U.S. Pat. Nos. 3,615,289 and 3,645,705 describe the formulation of candles. U.S. Pat. Nos. 3,148,125 and 5,538,718 describe the formulation of lipstick and other cosmetic sticks. U.S. Pat. Nos. 4,275,054, 4,937,069, 5,069,897, 5,102,656 and 5,500,209 each describe the formulation of deodorant and/or antiperspirant.

The gels of the present invention containing an active ingredient may additionally contain optional ingredients. The optional ingredients may serve one or more purposes, such as to facilitate the formation of a homogeneous gel, enhance the delivery properties of the product increase the aesthetic appeal of the product, enhance the ability of the product to release active ingredient, etc.

One suitable optional ingredient is a colorant. The addition of colorant to a gel which will be applied to skin or other surface will provide a marker so that the residue of the gel will be visible on the surface. A preferred fragranced stick or gel, absent the colorant, is clear and transparent, although the fragranced stick or soft gel of the present invention may be opaque or translucent. In any event, the addition of colorant may enhance the visual appeal of the fragranced stick or gel, and the residue provided when the stick or gel is rubbed across a surface. The colorant may be a dye or a pigment, and is preferably non-irritating to the skin when the gel will be applied to skin. Such colorants are well known in the art, and are used in, for example, cosmetics such as lipstick and eye shadow.

When present, the colorant is typically needed in only small amounts, for example, less than 5 wt. %, and often as little of 1 wt. % or even 0.1 wt. % is sufficient to impart a desired coloration to the gel. If a more intense coloration is desired, then the amount of colorant in the gel may be increased. When coloration is desired, the colorant should be present in an amount effective to provide the desired coloration.

Other optional components may serve to enhance the processing of the gel with the active ingredient. For example, the optional component may facilitate formation of a homogeneous mixture between the polyamide-polyether copolymer gellant and the active ingredient. In addition, the optional component will typically influence the consistency of the gel, and can be used to impart enhanced delivery properties to the stick or gel. For instance, in some cases the incorporation of volatile hydrocarbon or alcohol may enhance the homogeneity of the gel-active ingredient combination, as well as promote the delivery of a thin layer of gel to the skin, with the absence of a concomitant wet residue that might otherwise be present.

The copolymers of the present invention may be used to prepare gelled compositions useful as waxes and polishes, and the present invention provides a method of imparting a shiny appearance to a substrate using a copolymer of the present invention. Details of the preparation of such compositions, and the use of such compositions, are found in Document No. PCOM000009045D, accessed through www.ip.com, where the copolymers of the present invention may be used in lieu of, or in combination with, the gellants disclosed in this document. Basically, by utilizing a gellant component, wax and polish compositions which impart outstanding gloss, outstanding mar- and water-resistance, and minimal dirt pick-up to applied substrates can be prepared using the copolymers of the present invention. These compositions exhibit adhesion to polyurethane top-coats common in today's automotive finish market. Surprisingly, compositions exhibiting these properties can be generated very simply, requiring a formulation containing as few as 2 or 3 components, and nothing other than heat and a simple stirring motor to assemble a composition that is homogeneous in appearance, and gel-like, cream-like or paste-like in consistency. Thus, these compositions are easy to manufacture and make excellent waxes and polishes for furniture, automobiles, and other substrates. The wax and polish compositions contain gellant, solvent that is gelled by the gellant, and optional ingredients. These compositions are preferably homogeneous in appearance, cream-like, gel-like or paste-like in consistency, and easily applied to substrate surfaces. A paste form of the composition may include an aliphatic solvent, while an emulsion form of the composition may be prepared for liquid/cream applications. The gellants preferably have a non-crystalline structure (transparent) for excellent film formation and even (smooth) surface generation for high gloss development. UV stable and non-UV stable systems can be used for intermediate to long-lasting film integrity. The copolymer imbues the compositions with good hydrolytic stability at extreme ambient temperature and humidity. The waxes can demonstrate excellent water beading/repellency.

The copolymers of the present invention may be used to prepare gelled compositions useful as fire lighting fluids, and the present invention both provides such gelled compositions and provides methods of using such compositions as fire lighting fluids. Details of the preparation of such compositions, and the use of such compositions, are found in Document No. IPCOM000010393D, accessed at iwww.ip.com, where the copolymers of the present invention may be used in lieu of, or in combination with, the gellants disclosed in this document. Fire lighter fluids can be very efficient means of starting a fire. The low viscosity of these fluids can, however, impede a practical and safe usage. Gelation of these fluids is an elegant way to overcome these disadvantages. Currently such systems already exist for ethanol based systems and are highly successful. However, the low flash point of ethanol is still a point of concern, both in production as in application at the consumer level. The present invention provides for generating a gelled fire lighter system based on mineral oils and other fuels with a much higher and therefore safer flashpoint using the copolymer gelling agents of the present invention.

The copolymers of the present invention may be used to prepare gelled fiber reinforced plastic and gel coats. Details of the preparation of such compositions, and the use of such compositions, are found in Document No. IPCOM000007401 D, accessed at www.ip.com, where the copolymers of the present invention may be used in lieu of, or in combination with, the gellants disclosed in this document. Gelled matrix liquid compositions suitable for constructing fiber reinforced plastics and gel coats are hereby provided which comprise a matrix liquid and a copolymer of the present invention, the liquid being a mixture of one or more polymerizable monomers, an unsaturated polyester resin, a curing catalyst and optional components such solvent and inert filler and an organic polyamide gellant. The copolymer of the present invention is readily incorporated into the matrix liquid composition by mild heating and or high shear mixing to form, when cooled, a homogenous, shear-thinnable gel with thixotropic character that prevents separation of the liquid from the fiber matrix or sagging of the gel coat.

The copolymers of the present invention may be used to prepare gelled compositions useful for removing coatings from coated surfaces. Details of the preparation of such compositions, and the use of such compositions, are found in Document No. IPCOM000005738D, accessed at www.ip.com, where the copolymers of the present invention may be used in lieu of, or in combination with, the gellants disclosed in this document. Simply stated, organic coatings may be removed from their substrates by treating the coated substrate with a gelled organic solvent, where the gellant is, or includes, the copolymer of the present invention. For example, paint may be stripped from metal, wood, etc. by the process of contacting the paint with a gelled composition formed from turpentine or other organic solvent in combination with the copolymer of the present invention. The coating dissolves into the gel and/or the solvent from the gel is able to diffuse between the coating and the underlying substrate, thereby dissolving and/or loosening the coating so that the process of removing the gel also removes some or all of the coating. Multiple applications of gelled organic solvent may be needed to completely remove the coating. A gel is particularly advantageous when the coated surface is vertically positioned because the gel will resist running down the coated surface, and accordingly the gel will retain contact with the surface for as long as desired.

The articles of manufacture of the invention may be prepared by combining a polyamide-polyether copolymer as described herein with a suitable liquid and with the active ingredient(s), and heating these materials with stirring until a uniform mixture results. Upon cooling, the mixture will assume a gel or stick-like consistency.

The invention is illustrated in more detail by the following examples. In the following examples, chemicals were of reagent grade unless noted otherwise, and were obtained from commercial supply houses such as Aldrich Chemical Co. (Milwaukee, Wis., USA). DOWANOL™ glycol ethers are available from The Dow Chemical Co. (Midland, Mich., USA). DBE is "dibasic esters," any of a number of mixtures of the refined dimethyl esters of adipic, glutaric and succinic acids. DBE™ diesters, as well as Dytek® A diamine, are available from DuPont (Wilmington, Del., USA). EMPOL™ 1008 dimer acid is available from Henkel Corporation (Ambler, Pa., USA). EMEROX™ 1144 azelaic acid and VERSAMINE® amine compounds are available from Cognis Corporation (Cincinnati, Ohio, USA). XTJ amine compounds, JEFFAMINE® D-series diamines and M-series monoamines are available from Huntsman Performance Chemicals (Houston, Tex., USA).

EXAMPLES

Example 1

To a 500 mL flask was charged these acids: 4.02 g (1.8 wt. % 14.2 eq. %) isostearic acid; 23.059 (10.3 wt. %/75.5 eq. %)

CHDA; and 20.66 g (9.3 wt. %/20.2 eq. %) EMPOL™ 1008 dimer acid. Also charged to the flask were these amines: 69.08 g (31.0 wt. %/68.4 eq. %) VERSAMINE™ 551 dimer diamine and 106.1 g (47.6 wt. %/129.9 eq. %) JEFFAMINE™ D-2000 with a small amount of 25% aqueous hypophosphorous acid (about 0.5 mL). This reaction mixture was heated over about 2 hours while being stirred under a vigorous stream of nitrogen to 220° C. and held at this temperature for an additional 4 hours, then poured. The product copolymer was clear with a light amber color, non-tacky, flexible, and had an acid number of 2.3, an amine number of 0.6, and a softening point of 139.0° C. In the screening gelation test described herein (15% solids), this copolymer formed clear, firm gels in poly(propylene glycol) (mol. wt. 425), dimethyl sulfoxide, ethyl lactate, DOWANOL™ EPH, 2-ethylhexyl acetate, methyl soyate, and dibasic ester (dimethyl adipate).

Example 2

To a 250 mL flask was charged 60.09 (50.8 wt. %/100.0 eq. % of acids) EMPOL™ 1008 dimer acid, 53.1 g (44.9 wt. %/24.3 eq. % of amines) JEFFAMINE™ D-2000, and 5.1 g (4.3 wt %/81.5 eq. % of amines) ethylene diamine with a small amount of 25% aqueous hypophosphorous acid (about 0.5 mL). This reaction mixture was heated over about 2 hours while being stirred under a vigorous stream of nitrogen to 220° C. and held at this temperature for an additional 4 hours, then poured. The product copolymer was clear with almost no amber color, non-tacky, flexible, and had an acid number of 1.6, an amine number of 2.1, and a softening point of 107.2° C. In the screening gelation test described herein (15% solids), this copolymer formed clear immobile gels in poly(propylene glycol) (mol. wt 425), ethoxyethyl propionate, ethyl lactate (soft), DOWANOL™ EPH, 2-ethylhexyl acetate, xylene, methyl soyate, isopropyl palmitate, d-limonene, and a slightly hazy gel in DBE.

Examples 3-8 and 1C

Cyclohexane Dicarboxylic Acid-Based Copolymers with PAODA

These examples describe the preparation of polyamide-polyether copolymers comprising 1,4-cyclohexane dicarboxylic acid (CHDA), dimer diamine and poly(alkyleneoxy)diamine (PAODA), following the procedure of Examples 1 and 2, and the resulting physical properties thereof. Copolymer was prepared according to the weight percentages shown in TABLE 1. The resulting product was allowed to cool to ambient temperature, and assessed for its physical properties as set forth in TABLE 1. In Table 1, Example 1C is a comparative example of a polyamide prepared without a polyether block.

TABLE 1

Composition And Physical Properties Of Cyclohexane Dicarboxylic Acid-Based Polyamide-Polyether Copolymers With PAODA

| | Formulation (Weight Percent) | | | | | | |
|---|---|---|---|---|---|---|---|
| | Ex. 1C | Ex. 3 | Ex. 4 | Ex. 5 | Ex 6 | Ex. 7 | Ex. 8 |
| COMPONENT: | | | | | | | |
| CHDA | 10.7 | 16.1 | 14.5 | 7.3 | 17.0 | 9.0 | 12.4 |
| Sebacic Acid | 12.2 | — | Trace | — | — | — | — |
| Adipic Acid | — | — | 9.7 | 11.7 | — | 18.0 | — |
| VERSAMINE ™ 551 dimer diamine | 73.6 | 45.5 | 35.5 | 68.4 | 37.0 | 45.0 | 26.9 |
| D-2000* PAODA | — | 35.7 | — | 10.0 | 46.0 | — | — |
| XTJ-502* | — | — | — | — | — | — | 60.0 |
| D-400* PAODA | — | — | 37.9 | — | — | — | — |
| D-230* PAODA | — | — | — | — | — | 25.0 | — |
| Isostearic Acid | 3.5 | 2.7 | 2.4 | 2.7 | — | 3.0 | 1.0 |
| PROPERTIES | | | | | | | |
| Acid # | 1.0 | 0.6 | 6.8 | n.d.** | 12.4 | 4.5 | 2.0 |
| Amine # | 4.3 | 1.7 | 0.9 | n.d. | 0 | 3.9 | 2.3 |
| Softening Pt (° C.). | 126.2 | 168.5 | 107.2 | n.d. | 168.7 | 123.8 | 167.1 |
| Tackiness | None | None | None | None | None | None | None |
| Hardness | Hard | Hard | Hard | Hard | Hard | Very Hard | Hard |
| Flexibility | Yes | Yes | Yes | Yes | Yes | Some | Yes |

*JEFFAMINE ™ D-series, from Huntsman Chemicals.
**n.d., not determined.

Examples 2C and 10-15

Cyclohexane Dicarboxylic Acid Based Polyamide Gellants with PAODA

These examples describe the ability of polyamide-polyether copolymers comprising 1,4-cyclohexane dicarboxylic acid (CHDA), dimer diamine and poly(alkyleneoxy)diamine (PAODA), to form gels upon admixture with various liquid solvents. To test for gelation efficacy, about 0.6 grams of copolymer and about 3.4 grams of liquid were charged to a test tube before being capped with aluminum foil. The test tube was placed in an oven at about 115° C. and incubated for about 1 hour. The tube was then removed, agitated while still hot on a vortex stirrer briefly to ensure good copolymer contact with the solvent, and returned to the oven. After incubation for about 1 additional hour, the tube was removed and allowed to cool to ambient temperature. Tubes containing copolymers not fully dissolved after this treatment were placed in an oven about 10° C. warmer, and the procedure was repeated until the copolymer was fully dissolved. The sample was then removed from the oven and allowed to cool.

The cooled copolymer solution is then rated for gel quality as follows: "gel" means that the solution does not flow or slump when inverted and shaken strongly; "jelly" refers to a solution that slumps or cracks when shaken; "paste" refers to a mixture that is soft, hazy to very cloudy and inhomogeneous, where a paste slumps or flows when inverted; "2-phase" means that the copolymer dissolves in a hot solvent but separates from the solvent upon cooling to form two cloudy/hazy phases; "incompatible" means that the copolymer does not dissolve in hot solvent, but instead forms a separated solid top layer; "soluble" means that the mixture of copolymer and solvent form a clear and fluid solution.

The clarity of the cooled copolymer solutions may be characterized as follows: "crystal clear" means that one can see through the solution very easily, and the solution is essentially transparent; "hazy" means that the solution is not clear but print (e.g., newsprint) is legible when viewed through the solution, where modifiers include "very," "slight," and "very slight;" and "cloudy" means that one cannot see through the solution at all, where modifiers include "very," "slight," and "very slight."

Using these criteria, test tubes charged with copolymer and liquid, and the resulting mixtures were characterized with the results shown in TABLE 2. Comparative examples are denoted by "C" following the example number.

TABLE 2

Summary Of Gelation Test Results For Cyclohexane Dicarboxylic Acid-Based Polyamides With PAODA

| | | | Example | | | | |
|---|---|---|---|---|---|---|---|
| | 2C | 9 | 10 | 11 | 12 | 13 | 14 |
| | | | | Example | | | |
| | #1C | #5 | #7 | #3 | #4 | #6 | #8 |
| Co-Diacid | Sebacic | Adipic | Adipic | None | Adipic | None | None |
| PAODA* | None | D-2000 | D-230 | D-2000 | D-400 | D-2000 | XTJ-502 |
| Total PAO Wt % | 0.0 | 10.0 | 25.0 | 35.7 | 37.9 | 46.0 | 60.0 |
| TEST LIQUID | | | | | | | |
| DMSO | — | — | — | — | — | — | Gel |
| DOWANOL ™ EPH | 2 phase | 2 phase | Soluble | Slightly hazy gel | Soluble | n.d. | n.d. |
| N-Methyl Pyrrolidinone | 2 phase | 2 phase | Soluble | Slightly hazy gel | Soluble | Gel | Gel |
| DOWANOL ™ DPM | 2 phase | Cloudy gel | Hazy gel | Slightly hazy gel | Jelly | Gel | Gel |
| Ethyl Lactate | n.d. | 2 phase | Hazy gel | — | Soluble | Gel | Gel |
| Dibutyl Adipate | 2 phase | Incompatible | 2 phase | Hazy gel | Cloudy gel | Gel | n.d |
| 2-EthylHexyl Acetate | n.d | n.d. | n.d. | n.d. | n.d. | Gel | Cloudy Gel |

*JEFFAMINE ™ D-series, from Huntsman Chemicals.

Examples 15-18

Dimer Acid-Based Copolymers

These examples describe the preparation of polyamide-polyether copolymers comprising dimer acid and poly(alkyleneoxy)diamine, and the resulting physical properties thereof. These copolymers were prepared according to the procedure of Example 1. Composition and physical properties are shown in TABLE 3.

TABLE 3

Composition And Physical Properties Of Dimer Acid-Based Polyamide Copolymers

| | Formulation (Weight Percent) | | | |
|---|---|---|---|---|
| | Ex. 15 | Ex. 16 | Ex. 17 | Ex. 18 |
| COMPONENT | | | | |
| EMPOL ™ 1008 dimer acid# | 62.3 | 62.1 | 59.4 | 54.4 |
| EMEROX ™ 1144 azelaic acid# | — | — | 2.3 | — |
| D-2000 PAODA* | 30.0 | — | 29.9 | 39.6 |
| XTJ-502 PAODA* | — | 30.1 | — | — |
| Ethylene Diamine | 5.7 | 5.8 | 6.3 | 4.6 |
| Isostearic Acid | 2.0 | 2.0 | 2.1 | 1.5 |
| PROPERTIES | | | | |
| Acid# | 11.7 | 8.2 | 7.1 | 5.5 |
| Amine# | 1.3 | 0.6 | 1.1 | 0.5 |
| Dropping/ Softening Pt (° C.) | 104.0 | 105.3 | 147.9 | 100.5 |
| Tackiness | None | None | None | None |
| Hardness | Slightly soft | Hard | Hard | Hard |
| Flexibility | Yes | Yes | Yes | Yes |

TABLE 3-continued

Composition And Physical Properties Of Dimer Acid-Based Polyamide Copolymers

| | Formulation (Weight Percent) | | | |
|---|---|---|---|---|
| | Ex. 15 | Ex. 16 | Ex. 17 | Ex. 18 |
| Clarity | Light | Pale yellow | Pale yellow | Very light |

EMOREX ™ and EMOROL ™ are trademarks of Cognis Corp., Cincinnati, OH.
*Polyether diamine products from Huntsman Chemicals.

Examples 19-22

Dimer Acid-Based Polyamide Gellants

These examples describe the ability of polyamide-polyether copolymers comprising dimer acid and poly(alkyleneoxy)diamine, to form gels upon admixture with various solvents. These solvent/copolymer mixtures were prepared and characterized as described in Examples 10-15. Findings are summarized in TABLE 4.

TABLE 4

SUMMARY OF GELATION TEST RESULTS FOR DIMER ACID-BASED POLYAMIDES

| | Example | | | |
|---|---|---|---|---|
| | 19 | 20 | 21 | 22 |
| Example | 15 | 17 | 18 | 16 |
| Wt % | 30.0 | 29.9 | 39.6 | 30.0 |
| PAODA | D-2000 | D-2000 | D-2000 | XTJ-502 |
| SOLVENT: | APPEARANCE OF PRODUCT MIXTURE: | | | |
| DOWANOL ™ EPH | Gel | — | — | — |
| N-Methyl Pyrrolidinone | Gel | Slightly hazy gel | Weak gel | Gel |
| Xylene | Gel | — | Weak gel | — |
| DOWANOL ™ DPM | Gel | Gel | Gel | Slightly hazy gel |
| Ethyl Lactate | Slightly hazy gel | Slightly hazy gel | Gel | Slightly hazy gel |
| Dibutyl Adipate | Pasty | Cloudy gel | Hazy gel | Slightly hazy gel |
| Ethoxyethyl Propionate | — | — | Gel | — |
| Dichloroethane | — | — | Gel | — |
| Ethyl Hexyl Acetate | — | Slightly hazy gel | Gel | 2 phase |

— means experiment not performed or material not used

Example 23

Cyclohexane Dicarboxylic Acid-Based Polyamide-Polyether Gellants Containing Dimer Acid Polyamide-polyether copolymer was prepared according to the procedure of Example 1 using the weight percentages of reactants shown in TABLE 5. The resulting copolymer was a flexible, light amber, slightly soft, clear polymer, having a softening point of 132.8° C., an acid number of 5.2, and an amine number of 2.1.

Following admixture and incubation of this polyamide-polyether copolymer with solvent according to the procedure indicated in EXAMPLES 10-15, it was determined that this copolymer formed firm gels when combined with any of the following three solvents: dimethyl sulfoxide, DOWANOL™ DPM dipropylene glycol methyl ether (Dow, Midland, Mich., USA), or ethyl lactate.

TABLE 5

Polyamide-Polyether Copolymer Composition

| Component | Weight Percent |
|---|---|
| 1,4-Cyclohexane Dicarboxylic Acid | 16.4 |
| EMPOL ™ 1008 Dimer Acid | 11.0 |
| Propionic Acid | 0.8 |
| VERSAMINE ™ 551 Dimer Diamine | 31.6 |
| HUNTSMAN ™ XT-500 Poly(alkyleneoxy) Diamine | 40.2 |

Example 24

Dimer Acid-Based Polyamide-Polyether Gellants Containing a Poly(Butyleneoxy)Diamine Polyamide-polyether copolymer was prepared according to the procedure used in Example 1, using the weight percentages of reactants shown in TABLE 6. The resulting copolymer was a flexible, very light-colored, slightly soft, clear polymer, having a softening point of 100.1° C., an acid number of 9.4, and an amine number of 1.9.

Following admixture and incubation of this polyamide-polyether copolymer with solvent according to the procedure indicated in EXAMPLES 10-15, it was determined that this copolymer formed firm gels when combined with any of the following liquids: ethoxyethylpropionate, DOWANOL™ DPM dipropylene glycol methyl ether (Dow, Midland, Mich., USA), xylene, 2-ethylhexyl acetate, d-limonene, and methyl soyate.

TABLE 6

Polyamide-Polyether Copolymer Composition

| Component | Weight Percent |
|---|---|
| EMPOL ™ 1008 Dimer Acid | 51.1 |
| Ethylene Diamine | 4.0 |
| HUNTSMAN ™ XT-523 Poly(butyleneoxy) Diamine | 44.9 |

Example 25

Fragrance Stick

A gel base was first prepared by heating a mixture of 11.62 g of the copolymer of Example 1, 15.99 g of polypropylene glycol (MW=425), and 10.00 g of dimethyl adipate (DBE-6™ dibasic acid from Dupont, Wilmington, Del., USA) to 140° C., and holding at this temperature with stirring for about 20 minutes. This base was cooled to 110° C., at which temperature it was still a fluid. To this fluid was rapidly added 10.80 g (22.3 wt %) of a fragrance, namely "Country Comfort" (Product No. 446151 from Firmenich; Plainsboro, N.J., USA; www.firmenich.com), whereupon the temperature dropped to 82° C. After all of the fragrance was added, the liquid was poured (while still warm) into a 2" long×½" diameter cylindrical stick mold and allowed to thoroughly cool. The gel stick could be pressed out as needed from the container and smoothed out on the skin.

Example 26

Insect Repellant Stick

To a 250 mL flask was charged 46.4 g (46.4 wt. %/100.0 eq. % of acids) EMPOL™ 1008 dimer acid (Cognis Corp., Cincinnati, Ohio, USA), 50.0 g (50.0 wt. %/26 eq. % of amines) JEFFAMINE™ D-2000 diamine (Huntsman Chemical, Salt Lake City, Utah, USA), and 3.6 g (3.6 wt % 174 eq. % of amines) ethylene diamine (Aldrich, Milwaukee, Wis., USA), with a small amount of 25% aqueous hypophosphorous acid (about 0.5 mL). This reaction mixture was heated over about 2 hours while being stirred under a vigorous stream of nitrogen to 220° C. and held at this temperature for an additional 4 hours, then poured. The product copolymer was clear with almost no amber color, non-tacky although somewhat soft, and had an acid number of 2.2, an amine number of 2.1, and a softening point of 103.5° C. In the screening gelation test described herein (15% solids), this copolymer formed clear gels in DMSO, poly(propylene glycol) (mol. Wt. 425), NMP, ethyl lactate (soft), 2-ethylhexyl acetate (slightly hazy), xylene (soft), and propylene carbonate (slightly hazy).

This copolymer and diethyl-m-toluidine (DEET) were heated and stirred with other skin-friendly carrier components as show in TABLE 7 to about 130° C., except for the d-limonene (orange oil). After the components all formed a translucent, homogeneous blend, the blend was cool to about 100° C. and the d-limonene was added. The blend was poured while fluid and warm into 2" long×½" diameter cylindrical stick molds and allowed to thoroughly cool. The gel stick could be pressed out as needed from the container and spread on the skin by rubbing. However, the amount of gel not used but protruding out of the holder held its shape.

TABLE 7

Insect Repellant Stick Composition

| Component | Weight (g) | Weight % |
| --- | --- | --- |
| DEET | 1.83 | 11.14 |
| Ex. 43 Copolymer | 4.21 | 25.64 |
| Polypropylene Glycol, MW = 425 | 5.50 | 33.50 |
| 2-Octyldodecanol | 2.07 | 12.61 |
| Glycerol | 1.11 | 6.76 |
| d-Limonene | 1.70 | 10.35 |
| Total Weight | 16.42 | 100 |

Example 27

Make-Up Removal Gel Comprising a Copolymer Made with a Dihydric Alcohol

To a 250 mL flask was charged 20.0 g (17.7 wt. %/100.0 eq. % of acids) 1,4-cyclohexanedicarboxylic acid (CHDA, Eastman Chemical, Kingsport, Tenn., USA), 10.0 g (8.8 wt. %/21.5 eq. % of acid reactives) polyethyleneglycol (MW 400, Aldrich, Milwaukee, Wis., USA), 42.0 g (46.0 wt. %/18.1 eq. % of acid-reactives) JEFFAMINE™ D-2000 (Huntsman Chemical, Salt Lake City, Utah, USA), and 42.0 g (36.3 wt %/60.9 eq. % of acid-reactives) VERSAMINE™ 551 dimer diamine (Cognis Corp., Cincinnati, Ohio, USA) with a small amount of 25% aqueous hypophosphorous acid (about 0.5 mL). This reaction mixture was heated over about 2 hours while being stirred under a vigorous stream of nitrogen to 220° C. and held at this temperature for an additional 4 hours, then poured. The product copolymer was clear with an amber color, non-tacky, flexible, and had an acid number of 3.0, an amine number of nearly zero, and a softening point of 136.4° C. In the screening gelation test described herein (15% solids), this copolymer formed firm clear gels in DBE, poly (propylene glycol) (mol. Wt. 425), ethoxy ethyl propionate, ethyl lactate, and 2-ethylhexyl acetate, and a hazy gel in methyl soyate. This copolymer (1.00 g) was heated and stirred until homogeneous with SURFONIC™ L24-5 surfactant (HLB=10.6) and isopropyl myristate (4.75 g, 39.4%), cooled to about 100° C. and mixed with castor oil (1.44 g, 11.9%) and fragrance ("Foliage" from IFF, New York N.Y., USA, 0.21 g, 1.7%). The blend was poured while fluid and warm into a mold and allowed to thoroughly cool. It spread easily on the skin by rubbing and washed away easily with water.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A fragrance stick, gel, air freshener, cologne, fine fragrances, or perfume, comprising a copolymer, at least one surfactant having an HLB number of from 6 to 16, from 2 to 25 wt % of at least one fragrance, and from 0.1 to 5 wt % of colorant, wherein the copolymer comprises: a polyamide-polyether block copolymer formed from a reaction mixture comprising one or more diacid compounds comprising 1,4-cyclohexane dicarboxylic acid (CHDA) and one or more diamine compounds comprising poly(alkyleneoxy) diamine (PAODA), the reaction mixture containing at least one monofunctional compound reactive with amine groups wherein: a) the copolymer has a softening point that is at least 80.degree. C. and not more than 130.degree. C.; b) CHDA provides at least 60% of the acid equivalents from diacid compounds; and c) PAODA provides at least 50% of the amine equivalents from diamine compounds.

2. A fragrance stick, gel, air freshener, cologne, fine fragrance, or perfume, comprising a copolymer, at least one surfactant having HLB number of from 6 to 16, from 2 to 25 wt % of at least one fragrance, and from 0.1 to 5 wt % of colorant, wherein the copolymer comprises: a polyamide-polyether block copolymer formed from a reaction mixture comprising one or more diacid compounds comprising 1,4-cyclohexane dicarboxylic acid (CHDA) and one or more diamine compounds comprising poly(alkyleneoxy) diamine (PAODA), the reaction mixture containing at least one monofunctional compound reactive with carboxylic acid groups wherein: a) the copolymer has a softening point that is at least 80.degree. C. and not more than 130.degree. C.; b) CHDA provides at least 60% of the acid equivalents from diacid compounds; and c) PAODA provides at least 50% of the amine equivalents from diamine compounds.

3. A product selected from the group consisting of wax, polish and cleaner, comprising at least one polyamide-polyether block copolymer, water, and at least one liquid or at least one compound, wherein the at least one liquid or at least one compound comprises at least one ester chemical group, wherein the polyamide-polyether block copolymer comprises a softening point that is at least 80° C. and not more than 130° C.; and is formed from a reaction mixture of polymerized fatty acid and at least two diamine compounds comprising poly(alkyleneoxy) diamine (PAODA) and a short-chain aliphatic diamine (SDA) having from 2 to 6 carbon atoms, wherein further:
   a) for a reaction mixture comprising x grams of PAODA and y grams of SDA, the ratio $x/(x+y)$ is from 0.8 to 0.98 and
   b) for a reaction mixture weighing z grams, the ratio $x/z$ is >0.40.

4. The product according to claim 3, comprising from 5 to 50 wt % of the at least one polyamide-polyether block copolymer.

5. The product according to claim 3, wherein the wax, polish or cleaner is in the form of a cream, paste, or emulsion.

6. A composition, comprising at least one polyamide-polyether block copolymer, and at least one bioactive compound, wherein the polyamide-polyether block copolymer comprises a softening point that is at least 80° C. and not more than 130° C.; and is formed from a reaction mixture of polymerized fatty acid and at least two diamine compounds comprising poly(alkyleneoxy) diamine (PAODA) and a short-chain aliphatic diamine (SDA) having from 2 to 6 carbon atoms, wherein further:
   a) for a reaction mixture comprising x grams of PAODA and y grams of SDA, the ratio $x/(x+y)$ is from 0.8 to 0.98 and
   b) for a reaction mixture weighing z grams, the ratio $x/z$ is >0.40.

7. The composition according to claim 6, comprising from 5 to 50 wt % of the at least one polyamide-polyether block copolymer.

8. The composition according to claim 6, comprising from 5 to 50 wt % of the at least one polyamide-polyether block copolymer; and an effective amount of the at least one bioactive compound.

9. The composition according to claim 8, wherein the composition is an anti-insect article and wherein the at least one bioactive compound is at least one member selected from the group consisting of an insect repellent, an insecticide, and a pheromone.

10. The composition according to claim 6, wherein the at least one bioactive compound is at least one member selected from the group consisting of a cosmetic agent, a dermatological agent, an anti-itching agent, a topical analgestic, an anti-fungal agent, an antibiotic compound, a hemorrhoid treating compound, a wound-healing aid, an antioxidant, and an anti-acne agent.

11. The composition according to claim 10, wherein the at least one bioactive compound is at least one member selected from the group consisting of acetylsalicylic acid, acyclovir, 6-[3-(1-adamantyl)-4-methoxyphenyl]-2naphthoic acid, amphotericin B, ascorbic acid, benzoyl peroxide, betamethasone valerate, chloroxylenol, citric acid, clindamycin phosphate, clobetasol propionate, cyproheptadine, diclofenac, diphenylhydramine hydrochloride, econazole, erythromycin, estradiol, glycolic acid, glycyrrhetinic acid, hydrocortisone, hydroquinone, ibuprofen, ketoconazole, kojic acid, lactic acid, lidocaine hydrochloride, metronidazole, miconazole, miconazole nitrate, octopirox, 5-n-octanoylsalicylic acid, paracetamol, pramoxine hydrochloride, progesterone, salicylic acid, superoxide dismutases, terbinafine, thenaldie, tolnaftate, trimeprazine, 1,8,10-tripropionyl-9-anthrone, undecylenate, vitamin D, camphor, capsicin, menthol, methyl salicylate, trolamine salicylate, clotrimazole, miconazole nitrate, chloroxylenol, pyruvic acid, pharmaceutically acceptable salts of pyruvic acid, vitamin A, derivatives of vitamin A, derivatives of vitamin E, and benzoyl peroxide.

12. The composition according to claim 9, wherein the at least one bioactive compound comprises DEET.

13. The composition according to claim 11, wherein the at least one bioactive compound comprises retinoic acid, retinol, tocopherol or a combination thereof.

* * * * *